United States Patent
Mrva et al.

(10) Patent No.: US 7,865,250 B2
(45) Date of Patent: *Jan. 4, 2011

(54) METHODS FOR ELECTRICAL STIMULATION OF NERVES IN ADIPOSE TISSUE REGIONS

(75) Inventors: Joseph J. Mrva, Euclid, OH (US); Robert B. Strother, Willoughby Hills, OH (US); Geoffrey B. Thrope, Shaker Heights, OH (US); Julie Grill, Chapel Hill, NC (US); Maria E. Bennett, Lyndhurst, OH (US)

(73) Assignee: Medtronic Urinary Solutions, Inc., Minneapolis, MN (US)

( * ) Notice: Subject to any disclaimer, the term of this patent is extended or adjusted under 35 U.S.C. 154(b) by 1076 days.

This patent is subject to a terminal disclaimer.

(21) Appl. No.: 11/290,736

(22) Filed: Nov. 30, 2005

(65) Prior Publication Data

US 2006/0173507 A1 Aug. 3, 2006

Related U.S. Application Data

(63) Continuation-in-part of application No. 11/150,419, filed on Jun. 10, 2005, now Pat. No. 7,343,202.

(60) Provisional application No. 60/578,742, filed on Jun. 10, 2004.

(51) Int. Cl.
*A61N 1/05* (2006.01)

(52) U.S. Cl. .................. 607/128; 607/39; 607/118

(58) Field of Classification Search ............... 607/128, 607/143, 38
See application file for complete search history.

(56) References Cited

U.S. PATENT DOCUMENTS

| 3,902,501 | A | * | 9/1975 | Citron et al. ............. 607/126 |
|---|---|---|---|---|
| 4,014,346 | A | | 3/1977 | Brownlee |
| 4,721,118 | A | * | 1/1988 | Harris .................... 607/128 |
| 5,144,946 | A | | 9/1992 | Weinberg |
| 5,350,413 | A | | 9/1994 | Miller |
| 5,634,462 | A | | 6/1997 | Tyler |
| 6,006,133 | A | | 12/1999 | Lessar |
| 6,092,531 | A | | 7/2000 | Chen |
| 6,181,973 | B1 | * | 1/2001 | Ceron et al. .............. 607/126 |

(Continued)

FOREIGN PATENT DOCUMENTS

EP 1 468 648 10/2004

(Continued)

OTHER PUBLICATIONS

PCT Search Report and Written Opinion dated Sep. 9, 2009.

*Primary Examiner*—Kennedy J Schaetzle
(74) *Attorney, Agent, or Firm*—Campbell Nelson Whipps LLC

(57) ABSTRACT

Systems provide a stimulation electrode assembly sized and configured for placement in an adipose tissue region to stimulate a nerve in the adipose tissue region comprising an elongated lead sized and configured to be implanted within the adipose tissue region, the lead including at least two electrically conductive portions to apply electrical stimulation to nerve tissue in the adipose tissue region, and at least two expandable anchoring structures deployable from the lead to engage adipose tissue and resist dislodgment and/or migration of the at least two electrically conductive portions within the adipose tissue region.

18 Claims, 24 Drawing Sheets

U.S. PATENT DOCUMENTS

| | | |
|---|---|---|
| 6,516,227 B1 | 2/2003 | Meadows |
| 6,999,819 B2 * | 2/2006 | Swoyer et al. ............... 607/117 |
| 7,187,983 B2 * | 3/2007 | Dahlberg et al. ............ 607/128 |
| 7,343,202 B2 * | 3/2008 | Mrva et al. .................... 607/41 |
| 7,499,758 B2 * | 3/2009 | Cates et al. ................. 607/126 |
| 2003/0004434 A1 | 1/2003 | Greco |
| 2005/0038491 A1 * | 2/2005 | Haack ........................ 607/126 |
| 2006/0122660 A1 | 6/2006 | Boveja |
| 2006/0149345 A1 | 7/2006 | Boggs |
| 2006/0195153 A1 | 8/2006 | Diubaldi |
| 2007/0100411 A1 * | 5/2007 | Bonde ........................ 607/126 |
| 2008/0065167 A1 | 3/2008 | Boggs |
| 2008/0071322 A1 * | 3/2008 | Mrva et al. .................... 607/41 |

FOREIGN PATENT DOCUMENTS

| | | |
|---|---|---|
| EP | 1 790 304 | 5/2007 |
| WO | WO 2005/122727 | 12/2005 |
| WO | WO 2006/133445 | 12/2006 |
| WO | WO 2005/544448 | 5/2008 |

\* cited by examiner

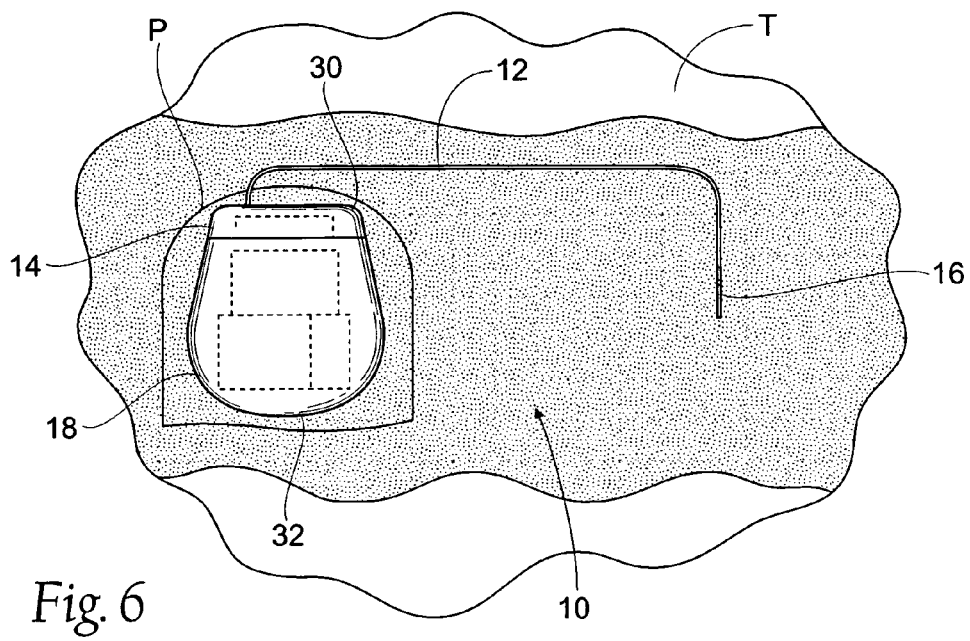
Fig. 6
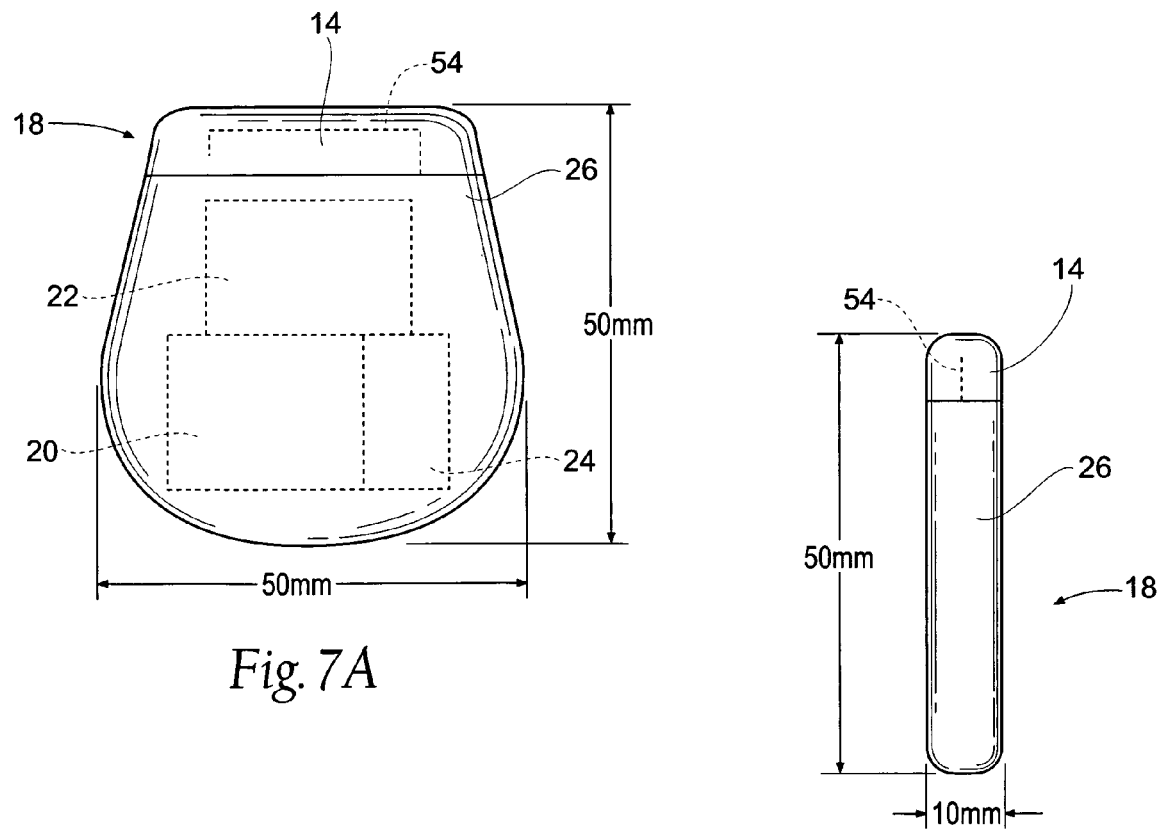
Fig. 7A
Fig. 7B

METHODS FOR ELECTRICAL STIMULATION OF NERVES IN ADIPOSE TISSUE REGIONS

RELATED APPLICATIONS

This application is a continuation-in-part of U.S. patent application Ser. No. 11/150,419, filed 10 Jun. 2005 (now U.S. Pat. No. 7,343,202), and entitled "Lead and Electrode Structures Sized and Configured for Implantation in Adipose Tissue and Associated Methods of Implantation." This application also claims the benefit of U.S. Provisional Patent Application Ser. No. 60/578,742, filed Jun. 10, 2004, and entitled "Systems and Methods for Bilateral Stimulation of Left and Right Branches of the Dorsal Genital Nerves to Treat Dysfunctions, Such as Urinary Incontinence," which are all incorporated herein by reference.

FIELD OF THE INVENTION

This invention relates to systems and methods for electrical stimulation on nerves in adipose tissue regions.

BACKGROUND OF THE INVENTION

I. Neuromodulation Stimulation

Neuromodulation stimulation (the electrical excitation of nerves, often afferent nerves, to indirectly affect the stability or performance of a physiological system) can provide functional and/or therapeutic outcomes. While existing systems and methods can provide remarkable benefits to individuals requiring neuromodulation stimulation, many limitations and issues still remain. For example, existing systems can often require the user to wear an external stimulator, which may provide a positive functional outcome, but may also negatively affect quality of life issues.

A variety of products and treatment methods are available for neuromodulation stimulation. As an example, neuromodulation stimulation has been used for the treatment of sexual dysfunction, which affects both men and women. A wide range of options exist for the restoration of sexual function. Treatments include everything from medications, simple mechanical devices, psychological counseling, external stimulators, and surgically implanted devices.

Both external and implantable devices are available for the purpose of neuromodulation stimulation for the restoration of sexual function. The operation of these devices typically includes the use of an electrode placed either on the external surface of the skin or a surgically implanted electrode. Although these modalities have shown the ability to provide a neuromodulation stimulation with positive effects, they have received limited acceptance by patients because of their limitations of portability, limitations of treatment regimes, and limitations of ease of use and user control.

II. Sexual Dysfunction

One form of male sexual dysfunction is know as Erectile Dysfunction (ED), and is often referred to as "impotency." There are some common diseases such as diabetes, Peyronie's disease, heart disease, and prostate cancer that are associated with impotency or have treatments that may cause impotency. And in some cases the cause may be psychological.

Erectile Dysfunction is common problem affecting men and is defined as the inability to achieve or maintain a penile erection sufficient for sexual activity. It is estimated that 35% to 50% of all men aged 40 to 70 have some form of ED, nearly 46 million Americans have ED, and over 150 million men have ED worldwide. It is also estimated that sexual dysfunctions occur in 43 percent of women in the United States. It would cost $3.5 billion per year if only one fifth of Americans with ED were treated with the first line of treatment (oral therapy such as PDE-5 inhibitors), and the cost for the second line of treatment (such as injection or transurethral administration of alprostadil) is approximately twice as expensive. A cost-effective therapy is needed because the number of men seeking treatment tripled between 1997 and 2000 and is expected to increase as awareness of treatment options for ED becomes more widespread.

The severity of erectile dysfunction can range from 1) mild ED, in which a man is occasionally unable to achieve and sustain an erection sufficient for intercourse, to 2) frequent or moderate ED to 3) severe or complete ED, in which a man is never able to produce and sustain an erection sufficient for intercourse. The prevalence of moderate to complete ED increases with age. Approximately 20% of men aged 40 years have moderate to severe ED and approximately 70% of men aged 70 years have moderate to severe ED. Over 70% of men with ED report that their quality of life is moderately to severely reduced by ED, and over 70% of men with ED feel hurt by the response of their partner to their ED and feel "to some extent a failure" because of their ED. Thus, ED is often associated with poor self-image, depression, and it can affect interpersonal relationships and lead to increased mental stress.

ED is often a result of a combination of psychological and organic factors, but it is thought to be purely psychological in origin in less than 30% of the cases. Organic factors can include complications from neurologic diseases (stroke, multiple sclerosis, Alzheimer's disease, brain or spinal tumors), chronic renal failure, prostate cancer, diabetes, trauma, surgery, medications, and abnormal structure. However, most cases of ED are associated with vascular diseases. An erection cannot be sustained without sufficient blood flow into and entrapment within the erectile bodies of the penis, and vascular related ED can be due to a malfunction of either the arterial or the venous system.

In a healthy individual, penile erection is generated by increased blood low into the penis via arterial dilation and decreased blood flow from the penis via venous occlusion. Arterial dilation is generated by activation of the cavernous nerve (a parasympathetic nerve), which causes relaxation of corporeal smooth muscle of the cavernosal and trabecular spaces. Penile erection begins with the filling and expansion of the three erectile bodies: the corpus spongiosum and the two corpora cavernosa. This expansion compresses the venules, preventing blood from leaving the penis and furthering the erection.

Persons with vasculogenic erectile dysfunction are unable to achieve penile erection due to either insufficient arterial blood flow or insufficient venous occlusion or both. Normal reflex erection coordinates dilation of penile blood vessels, augmenting vascular filling, and venous occlusion, preventing leakage and increasing penile stiffness.

Stimulation of a target nerve N, such as the dorsal nerve of the penis (DNP) afferents activates spinal circuitry that coordinates efferent activity in the cavernous nerve (CN), increasing filling via dilation of penile arteries, and efferent activity in the pudendal nerve (PN), preventing leakage via occlusion of penile veins, producing a sustained reflex erection (see FIG. 1)

FIGS. 2 and 3 show a profile and cross-section of the penis, illustrating the anatomical relationship of the erectile tissue (corpora cavernosa and corpus spongiosum) inside the penis. FIGS. 4 and 5 show the physiological changes in the size of the penile arteries, erectile tissue, and veins during erection. FIG. 4 shows the penile arteries constricted, the erectile tissue collapsed, and the veins open prior to an erection. Arterial dilation leads to increased inflow of blood, which fills and expands the erectile tissue as the veins are compressed to decrease outflow of blood from the erectile tissue, as shown in FIG. 5.

III. Methods of Treatment For ED

Methods of treatment for erectile dysfunction are available but are either often discontinued due to loss of efficacy or side effects or reserved as a final recourse requiring irrevocable damage. Three lines of treatment exist for ED. Oral therapy (PDE-5 inhibitors) is usually the first line of treatment, and it can be effective in up to 70% of men when it is first administered, but half of the patients stop taking PDE-5 inhibitors because they lose their effectiveness within one to three years. The second line of treatment is usually a minimally invasive therapy such as a vacuum device or direct administration of a vasoactive agent. The second-line treatments are usually effective in 33% to 70% of men, but they are also later discontinued by over half of the patients, often due to side effects such as pain or local damage at the site of administration. For the 30% to 65% of men who fail or discontinue oral therapy, the total cost for the second line of treatment (vacuum device or alprostadil, administered via injection or transurethrally) would be $1 to $6 billion. However, side effects of pain and local damage are associated with the second line of treatment, and at least half of the men discontinue this form of therapy. If the men who failed or discontinued both the first and second lines of treatment chose to receive a penile prosthesis, the total cost would be over $20 billion. Yet, implantation of a penile prosthesis is reserved for the final method of treatment because the implantation causes permanent (irrevocable) damage to the erectile tissue resulting in the loss of any future erection if the implant is removed. Thus, an alternative approach is needed that can provide a multitude of advantages over the current therapies.

IV. Neuromodulation Stimulation to Evoke Erection

Systemic side effects (headache, flushing, dyspepsia, etc.) and permanent damage to the corpora cavernosa may be avoided by electrically stimulating a peripheral nerve to activate a reflex that coordinates arterial dilation with venous occlusion, producing an erection. In anesthetized, spinalized rats, electrical stimulation of afferent pathways in the dorsal nerve of the penis (DNP) can produce an increase in corpus cavernous pressure (CCP). The increase in CCP is gated to the onset and offset of stimulation and has been sustained for up to fifteen minutes. Previous results in the dog demonstrated that reflex erections are repeatable for a period of three to five hours. Stimulation of the DNP leads to transient increases in the EMG activity of the ischiocavernosus (IC) and bulbospongiosus (BS) muscles, which are responsible for venous occlusion. Venous occlusion prevents leakage of blood from the penis and explains why DNP stimulation can evoke suprasystolic increases in penile pressure. These animal experiments demonstrate that DNP stimulation can evoke a reflex erection, but they do not determine if the reflex erection is comparable to the erections evoked by the present treatment methods.

An implantable stimulation system is needed that can provide an erection quickly and is acceptable to men who use or may need to use nitrates to treat cardiovascular disease because over 35% of men with cardiovascular disease develop ED. The loss of efficacy of oral therapy is likely due to the long duration (four to eighteen hours) of action, and the consistently elevated drug concentrations can reduce the response to the drug via tachyphylaxis or increased tolerance as seen with nitroglycerin tolerance. No loss of efficacy is expected with an implantable stimulation system that will only be activated five minutes before and during erection, and it will provide controlled release of neurotransmitter via activation of a reflex in the central nervous system.

The implantable stimulation system may be activated by the movement of a magnet over a magnetic reed switch within the implantable pulse generator of the stimulation system, or the press of a remote button, for example. Unlike the second line of treatment, this approach will not require a constrictive ring, needle insertion, or urethral-suppository insertion, which can cause local injury prior to each erection and lead to discontinuation of treatment. In contrast to the penile implant, an implantable stimulation system approach will not damage the erectile tissue.

There remains a need for systems and methods that can effectively restore sexual function, in a straightforward manner, without requiring drug therapy and complicated (and in some instanced irrevocable) surgical procedures.

SUMMARY OF THE INVENTION

One aspect of the invention provides systems and methods for a stimulation electrode assembly sized and configured for placement in an adipose tissue region to stimulate a nerve in the adipose tissue region. The stimulation electrode assembly includes an elongated lead sized and configured to be implanted within the adipose tissue region, the lead including at least two electrically conductive portions to apply electrical stimulation to nerve tissue in the adipose tissue region. Each electrically conductive portion may comprise a conductive surface area in the range of about 10 mm$^2$ to about 20 mm$^2$. The at least two electrically conductive portions can be configured to function as two individual stimulating electrodes in a monopolar configuration or as one stimulating electrode in a bipolar configuration.

The lead also includes at least two expandable anchoring structures deployable from the lead to engage adipose tissue and resist dislodgment and/or migration of the at least two electrically conductive portions within the adipose tissue region. Each expandable anchoring structure may include two circumferentially spaced-apart, radiating shovel-like blade shaped members. These two shovel-like blade shaped members may be spaced 180 degrees apart and the at least two expandable anchoring structures may be spaced 90 degrees apart.

An additional aspect of the invention provides systems and methods for stimulation of a nerve in an adipose tissue region by providing a stimulation electrode assembly comprising an elongated lead sized and configured to be implanted within the adipose tissue region, the lead including at least two electrically conductive portions to apply electrical stimulation to nerve tissue in the adipose tissue region, and at least two expandable anchoring structures deployable from the lead to engage adipose tissue and resist dislodgment and/or migration of the at least two electrically conductive portions within the adipose tissue region, implanting the stimulation electrode assembly in an adipose tissue region, and conveying electrical stimulation waveforms through the stimulation electrode assembly to achieve selective stimulation of at least one nerve in the adipose tissue region.

The stimulation electrode assembly may be implanted at or near a pubic symphysis wherein the stimulation stimulates a left and/or right branch of the dorsal genital nerves.

An additional aspect of the invention provides systems and methods for stimulation of a target nerve in an adipose tissue region comprising a stimulation electrode sized and configured to be implanted in adipose tissue to stimulate the target nerve in a region at or near a pubic symphysis and an implantable pulse generator.

The stimulation electrode comprises an elongated lead sized and configured to be implanted within the adipose tissue region, the lead including at least two electrically conductive portions to apply electrical stimulation to nerve tissue in the adipose tissue region, and at least two expandable anchoring structures deployable from the lead to engage adipose tissue and resist dislodgment and/or migration of the at least two electrically conductive portions within the adipose tissue region, and The implantable pulse generator is sized and configured to be positioned subcutaneous to a tissue surface remote from the stimulation electrode, the implantable pulse generator comprising wireless telemetry circuitry, the wireless telemetry circuitry being functional within arms reach of the patient, and being adapted for programming and interrogation of the implantable pulse generator. The implantable pulse generator may be sized and configured to convey electrical stimulation waveforms to the stimulation electrode to stimulate a left branch and/or a right branch of the dorsal genital nerves.

Other features and advantages of the inventions are set forth in the following specification and attached drawings.

BRIEF DESCRIPTION OF THE DRAWINGS

FIG. 6 is a view of a stimulation assembly that provides electrical stimulation to central nervous system tissue, muscles and/or nerves inside the body using a general purpose implantable pulse generator.

FIGS. 7A and 7B are front and side views of the general purpose implantable pulse generator shown in FIG. 6, which is powered by a primary battery.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with the restoration of sexual function (e.g., erectile restoration) by the unilateral or bilateral stimulation of the left and/or right branches of the dorsal genital nerves using a lead or leads implanted in adipose or other tissue in the region at or near the pubic symphysis, or electrode(s) implanted on the left and/or right branches of the dorsal genital nerves. That is because the features and advantages of the invention are well suited for this purpose. Still, it should be appreciated that the various aspects of the invention can be applied in other forms and in other locations in the body to achieve other objectives as well. These objectives pertain to both male and female, human and animal, and may include, but are not limited to, erection, ejaculation, arousal, and lubrication.

I. System Overview

A. Neuromodulation Stimulation

Figure 1:
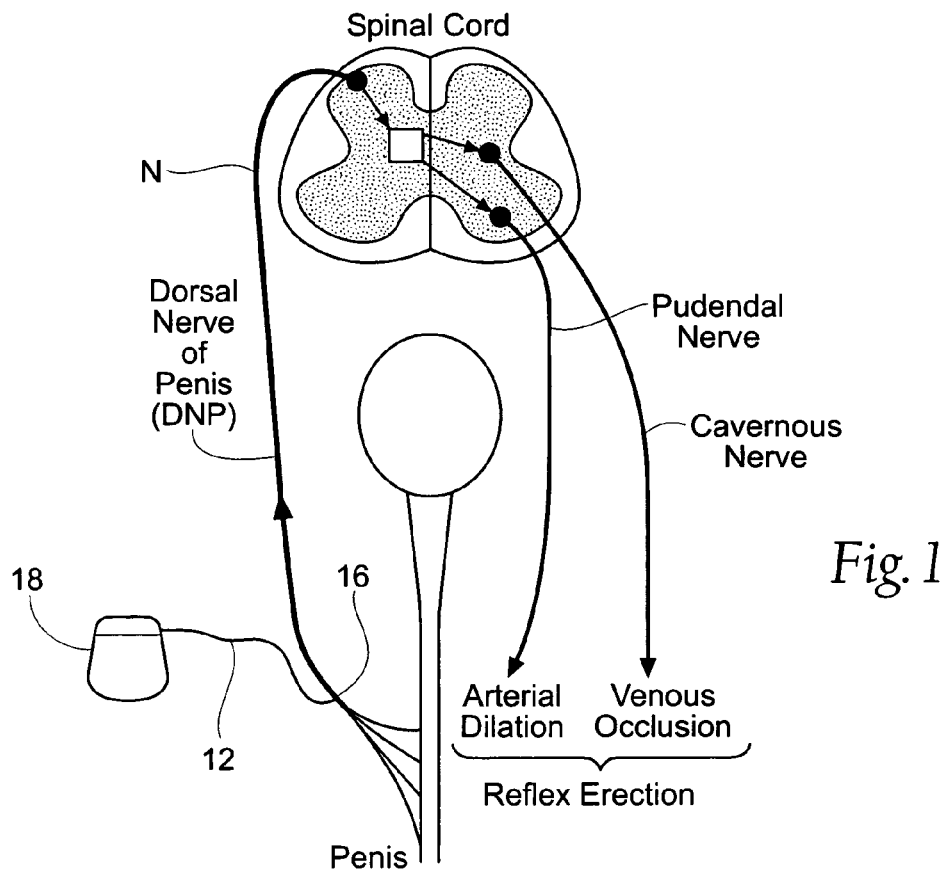
FIG. 1 is a schematic view of the stimulation of a target afferent nerve and the spinal circuitry activated to coordinate efferent nerve activity for sexual restoration.

Afferent stimulation produces a full penile erection by activating sensory fibers with a stimulation pattern that mimics the pattern of sensory signals sent to reflex circuitry during coitus. The reflex circuitry then coordinates the 1) increase in blood flow into the penis via dilation of penile arteries with the 2) decrease in blood flow exiting the penis via occlusion of penile veins (see FIG. 1).

The afferent pathway(s) may be activated by stimulation of any genital nerve including the dorsal penile nerve; the ilioinguinal nerve; the medial, lateral, and posterior scrotal branches of the perineal nerve; the cavernous nerve, the perineal branch of the posterior femoral cutaneous nerve, the dorsal clitoral nerve, the vaginal nerves, and the labial nerves, for example. These pathways may also be activated by stimulation of any spinal root which supplies any of these genital nerves. Any combination of the genital nerves and/or their spinal roots will be referred to as the target nerve N.

An implant system 10 will be used to provide electrical stimulation of a target nerve N (e.g., the dorsal nerve of the penis) to provide sustainable erections on-demand with a simple surgical procedure that preserves the existing anatomy.

The electrical stimulation may be applied with any type of electrical contact such as a lead 12 placed in, on, around, or near any of the target nerve N named above. Note that the electrode 16 may be in contact with the target nerve N, or it may be some distance (on the order of centimeters) away because it does not have to be in contact with the target nerve N to activate it.

Stimulation may be applied through a lead, such as a fine wire electrode, inserted via needle introducer in proximity of a target nerve N. When proper placement is confirmed, as indicated by patient sensation or visible movement of related organs, such as the penis, scrotum, or anal sphincter, (or clitoris for women), the needle may be withdrawn, leaving the electrode in place.

Alternatively, stimulation may be applied through any type of nerve cuff (spiral, helical, cylindrical, book, flat interface nerve electrode (FINE), slowly closing FINE, etc.) that is surgically placed on or around a target nerve N.

Stimulation may also be applied through a penetrating electrode, such as an electrode array that is comprised of any number ($\geq 1$) of needle-like electrodes that are inserted into a target nerve N.

In all cases, the lead 12 may be routed subcutaneously to an implantable pulse generator (IPG) 18. The IPG may be located some distance from the electrode 16 or it may be integrated with the electrode, eliminating the need to route the lead 12 subcutaneously.

Control of the stimulation parameters may be provided by an external controller. The IPG external controller (clinician programmer 36) may be a remote unit that uses wireless communication (such as RF or magnetic signals) to control the IPG 18. The implantable pulse generator 18 may use regulated voltage (10 mV to 20 V), regulated current (10 μA to 50 μA), and/or passive charge recovery to generate the stimulation waveform.

The pulse may by monophasic or biphasic. In the case of the biphasic pulse, the pulse may be symmetrical or asymmetrical. Its shape may be rectangular or exponential or a combination of rectangular and exponential waveforms. The pulse width of each phase may range between 10 μsec and 10 to the sixth power psec.

Pulses may be applied in continuous or intermittent trains (i.e. the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary in a random (or pseudo random) fashion. Varying the stimulus frequency and/or duty cycle may assist in warding off habituation because of the stimulus modulation.

The stimulating frequency may range from 1 to 300 Hz, and the frequency of stimulation may be constant or varying. In the case of applying stimulation with varying frequencies, the frequencies may vary in a consistent and repeatable pattern or in a random (or pseudo random) fashion or a combination of repeatable and random patterns.

B. The Implant System

FIG. 6 shows an implant system 10 for the restoration of sexual function in animals, including humans.

The system 10 includes an implantable lead 12 having a proximal and distal end coupled to an implantable pulse generator or IPG 18. The lead 12 and the implantable pulse generator 18 are shown implanted within a tissue region T of a human or animal body.

The distal end of the lead 12 includes at least one electrically conductive surface, which will in shorthand be called an electrode 16. The electrode 16 is implanted in electrical conductive contact with at least one functional grouping of neural tissue, muscle, or at least one nerve, or at least one muscle and nerve. The implantable pulse generator 18 includes a connection header 14 that desirably carries a plug-in receptacle (connector) for the lead 12. In this way, the lead 12 electrically connects the electrode 16 to the implantable pulse generator 18.

The implantable pulse generator 18 is sized and configured to be implanted subcutaneously in tissue, desirably in a subcutaneous pocket P, which can be remote from the electrode 16, as FIG. 6 shows. Desirably, the implantable pulse generator 18 is sized and configured to be implanted using a minimally invasive surgical procedure.

The lead 12 and electrode 16 are sized and configured to be implanted percutaneously in tissue, and to be tolerated by an individual during extended use without pain or discomfort. The comfort is both in terms of the individual's sensory perception of the electrical waveforms that the electrode applies, as well as the individual's sensory perception of the physical presence of the electrode and lead. In both categories, the lead 12 and electrode 16 are desirably "imperceptible."

Figure 8B:
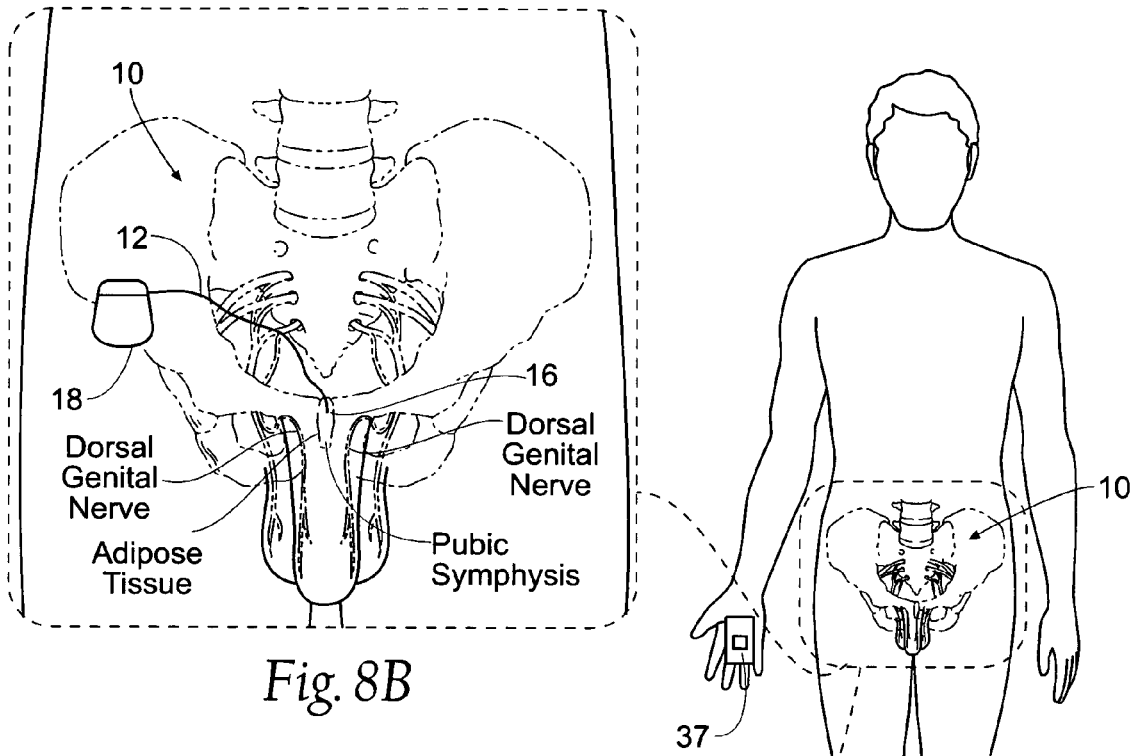
FIGS. 8A and 8B are anterior anatomic views of the system shown in FIG. 6 after implantation in an adipose tissue region at or near the pubic symphysis.
Figure 8C:
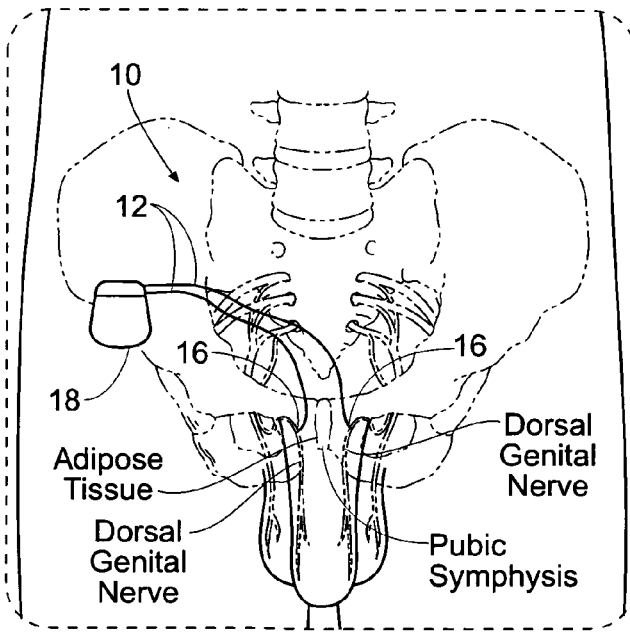
FIG. 8C is an anterior anatomic view of an alternative configuration of the system shown in FIG. 8B, showing more than one lead and electrode implanted in the targeted tissue region.
Figure 8A:
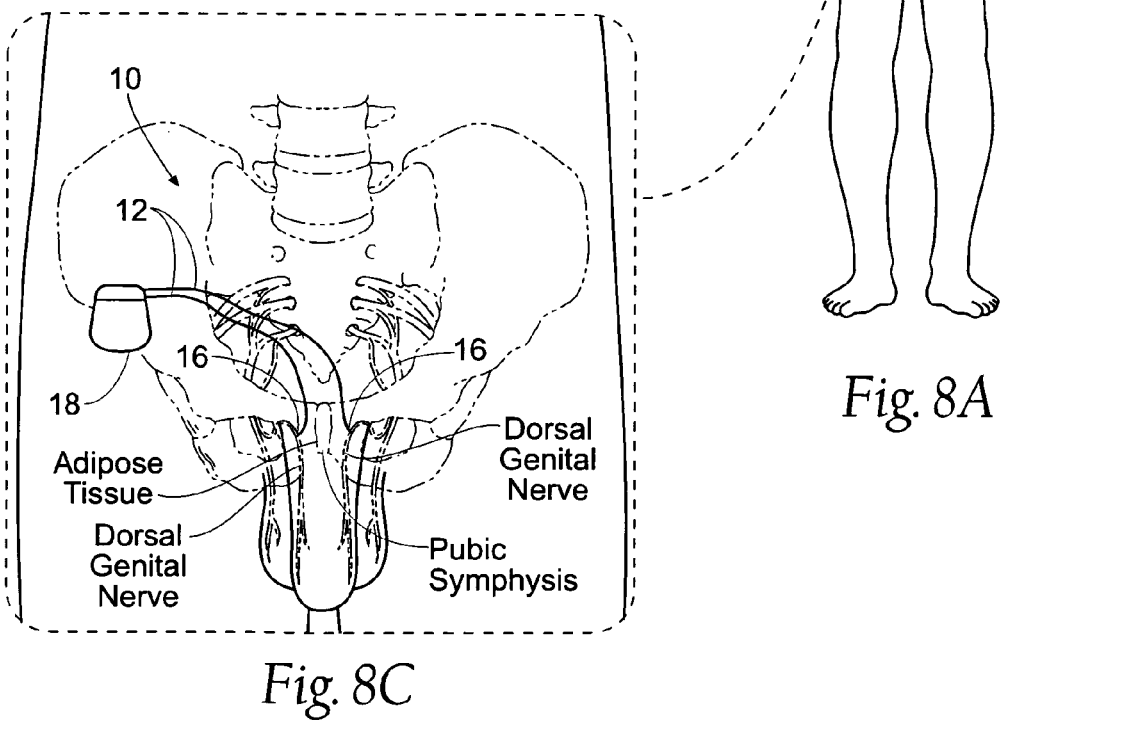

In particular, one configuration of the lead 12 and electrode 16 are sized and configured to reside with stability in soft or adipose tissue in the lower anterior pelvic region of the body (see FIGS. 8A and 8B). It has been discovered that, when properly placed in this region, one or more lead/electrode(s) 16 are uniquely able to deliver electrical stimulation current simultaneously to both left and right branches of the dorsal genital nerves, present near the clitoris in a female and near the base of the penis of a male (see FIGS. 8A and 8B). Specific features of the lead 12 and electrode 16 that make them well suited for this purpose, as well as other purposes, will be described in greater detail later.

As FIGS. 7A and 7B show, the implantable pulse generator 18 includes a circuit 20 that generates electrical stimulation waveforms. An on-board, primary battery 22 desirably provides the power. The implantable pulse generator 18 also desirably includes an on-board, programmable microcontroller 24, which carries embedded code. The code expresses pre-programmed rules or algorithms under which the desired electrical stimulation waveforms are generated by the circuit 20. The implantable pulse generator 18 may also include an electrically conductive case 26, which can also serve as the return electrode for the stimulus current introduced by the lead/electrode when operated in a monopolar configuration.

As shown in FIGS. 8A and 8B, the implantation site can comprise a tissue region on the posterior hip. Alternatively, the implantation site can comprise a more medial tissue region in the lower abdomen. There, the pulse generator 18 can reside for extended use without causing pain and/or discomfort and/or without effecting body image.

Figure 14:
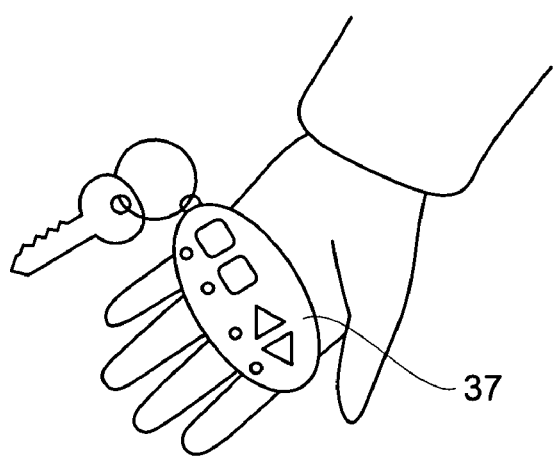
FIG. 14 is a perspective graphical view of one possible type of patient controller that may be used with the implantable pulse generator shown in FIGS. 7A and 7B.

The implant system 10 includes an external patient controller 37 (see FIGS. 8A and 14). The patient controller 37 is sized and configured to be held or worn by the individual to transcutaneously activate and deactivate or modify the output of the pulse generator 18. The patient controller 37 may, e.g., be a simple magnet that, when placed near the site where the pulse generator 18 is implanted (see FIG. 14), toggles a magnetic switch within the implantable pulse generator 18 between an on condition and an off condition, or advances through a sequence of alternative stimulus modes pre-programmed by the clinician into the implantable pulse generator 18. Alternatively, the patient controller 37 may comprise more sophisticated circuitry that would allow the individual to make these selections through an RF field (magnetic and/or electric) that passes through the skin and tissue within an arm's length distance (or up to two meters) from the implanted pulse generator 18.

According to its programmed rules, when switched on, the implantable pulse generator 18 generates prescribed stimulation waveforms through the lead 12 and to the electrode 16. These waveforms bilaterally stimulate the left and right branches of the dorsal genital nerves in a manner that achieves the desired physiologic response.

It has been discovered that bilateral stimulation of the dorsal genital nerves achieved by placement of a single electrode 16 at a unique location in the body (which will be described in greater detail later), achieves the desired physiologic result. Alternatively, more than one electrode may be placed to stimulate the dorsal genital nerves (e.g., one or more electrodes to stimulate the left branch and one or more electrodes to stimulate the right branch, see FIG. 8C). Bilateral stimulation may be achieved with a single electrode 16, but due to anatomical variations in the patient or possible target nerve N damage prior to and unrelated to implantation, the patient may be limited to unilateral stimulation of either the left or the right branches of the dorsal genital nerve, for example. Or, the physician may not be able to implant only one electrode 16 that can activate both branches of the dorsal genital nerve, but if both branches are healthy, then the physician will likely want to stimulate both branches. In this case the physician will implant two or more electrodes 16, one on, in, or near the left branch of the dorsal genital nerve and one on, in, or near the right branch of the dorsal genital nerve.

Using the controller 26, the individual may turn on or turn off the sexual restoration control waveforms at will or adjust the waveforms to achieve the desired functional restoration result. As previously discussed, erectile restoration is just one example of a functional restoration result. Additional examples of desirable therapeutic (treatment) or functional restoration indications will be described in greater detail in section "V. Representative Indications."

The system 10 desirably includes means for selectively varying the frequency or range of frequencies for a variable duration at which the stimulation waveforms are applied by the one or more electrodes 18. By modulating the frequency and/or duration of the stimulation waveform, the same system components and placement of electrodes can serve to achieve markedly different physiologic responses, and in addition, reduce habituation.

The shape of the waveform can vary as well. It can, e.g., be a typical square pulse, or possess a ramped shape. The pulse, or the rising or falling edges of the pulse, can present various linear, exponential, hyperbolic, or quasi-trapezoidal shapes. The stimulation waveform can be continuous, or it can be variable and change cyclically or in step fashion in magnitude and waveform over time.

In a non-limiting exemplary embodiment, the stimulus waveforms may include a variable frequency for a variable duration (e.g., a first stimulation at 5 Hz for 2 seconds, then 7 Hz for 3 seconds, then 6 Hz for 1 second, and so on), intermittent stimulation (apply stimulation in bursts separated by pauses in stimulation (e.g., stimulation for 3 seconds, rest for 2 seconds, repeat, and so on). The stimulus waveforms may also include a continuously or intermittently applied duty cycle of pulses. This may be considered the same as changing the frequency but it also refers to 1) the duration of bursts of stimulation and 2) the duration of pauses between the bursts. For example, a variable duty cycle for intermittent pulses may include stimulation with 10 pulses, then off for 500 milliseconds, stimulation with 15 pulses, then off for 750 milliseconds, stimulation with 5 pulses, then off for 2 seconds, and it could keep going in this variable pattern.

The stimulus waveforms may also include stimulation at different amplitudes. This may be beneficial because increasing the amplitude may increase penile tumescence to a certain degree, and then increasing the amplitude further may be used to cause ejaculation. Thus, amplitude modulation may be used to control the response. Varying the amplitude may also provide another form of anti-habituation control, allowing a sexual function (e.g., erection) to remain more robust than if the target nerve N was stimulated at a constant amplitude. Amplitude modulation may also more realistically recreate the varying level of fiber activation that occurs during coitus.

The patient controller 37 and/or a clinician programmer, for example, may include a manual-actuated switch or control knob which an operator operates or tunes to acquire a desired waveform frequency, given the desired physiologic response.

C. The Anatomic Landmarks

As already described, certain components of the implant system 10 are sized and configured to be implanted in adipose tissue in the lower anterior pelvic region, where it has been discovered that effective bilateral stimulation of both the left and right branches of the dorsal genital nerves can be achieved with one or more electrodes. The main anatomic landmark guiding the unique placement of these components is the pubic symphysis.

Figure 9:
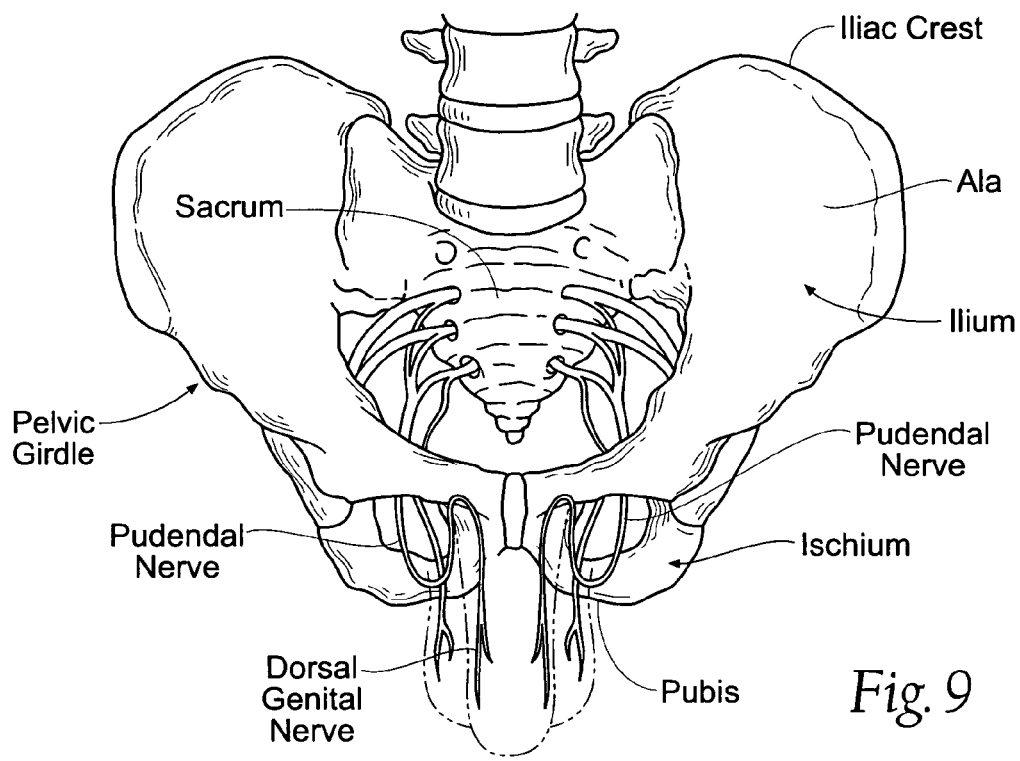
FIG. 9 is an anterior anatomic view of the pelvic girdle in a human.

As FIG. 9 shows, the hip bones are two large, irregularly shaped bones, each of which develops from the fusion of three bones, the ilium, ischium, and pubis. The ilium is the superior, fan-shaped part of the hip bone. The ala of the ilium represents the spread of the fan. The iliac crest represents the rim of the fan. It has a curve that follows the contour of the ala between the anterior and posterior superior iliac spines.

Figure 10:
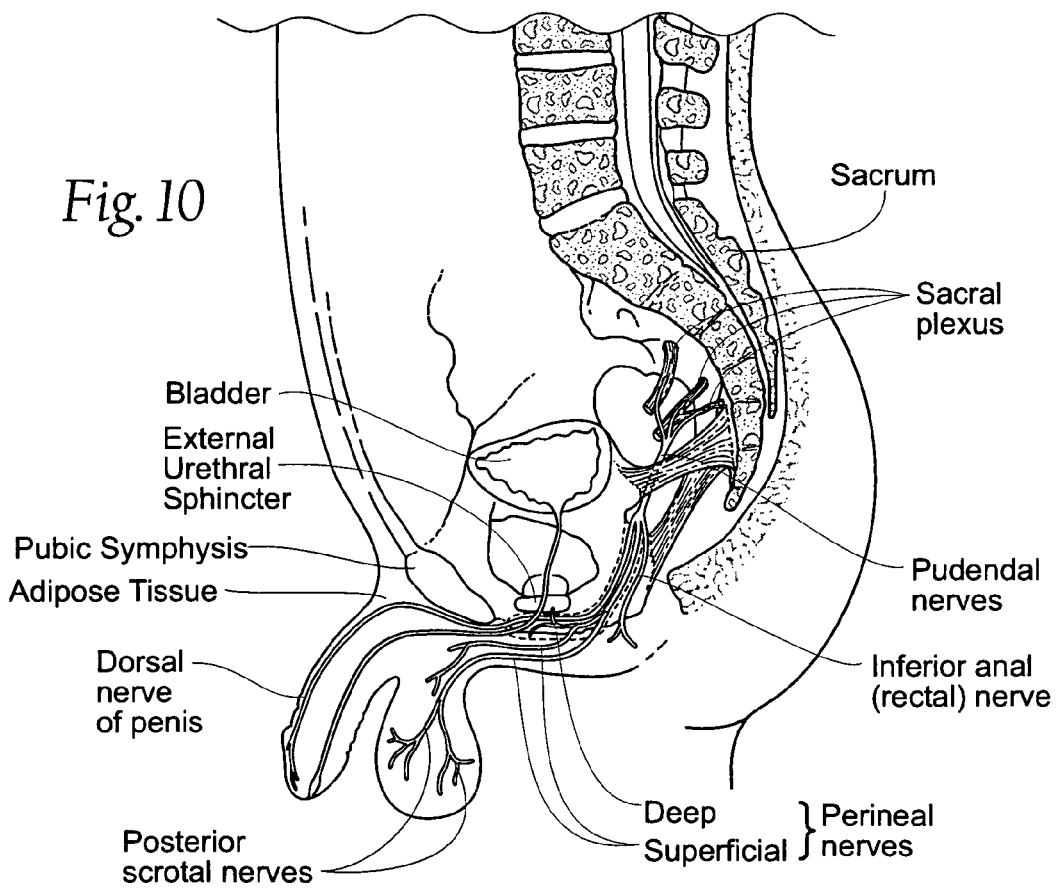
FIG. 10 is a lateral section view of the pelvic girdle region shown in FIG. 9.

As FIGS. 9 and 10 show, the sacrum is formed by the fusion of five originally separate sacral vertebrae. The hip bones are joined at the pubic symphysis anteriorly and to the sacrum posteriorly to form the pelvic girdle (see FIG. 9). The pelvic girdle is attached to the lower limbs. Located within the pelvic girdle are the abdominal viscera (e.g., the ileum and sigmoid colon) and the pelvic viscera (e.g., the urinary bladder and prostate gland for males, and the urinary bladder and reproductive organs such as the uterus and ovaries for females).

Within this bony frame (see FIGS. 9 and 10), the pudendal nerve is derived at the sacral plexus from the anterior divisions of the ventral rami of S2 through S4 and carries afferent (sensory) and efferent (motor) nerve components that innervate muscles and organs in the lower abdomen. The pudendal nerve extends bilaterally, in separate branches on left and right sides of the pelvic girdle. Each branch accompanies the interior pudendal artery and leaves the pelvis through the left and right greater sciatic foramens between the piriformis and coccygeus muscles. The branches hook around the ischial spine and sacrospinous ligament and enter the skin and muscles of the perineum through the left and right lesser sciatic foramen.

Figure 11:
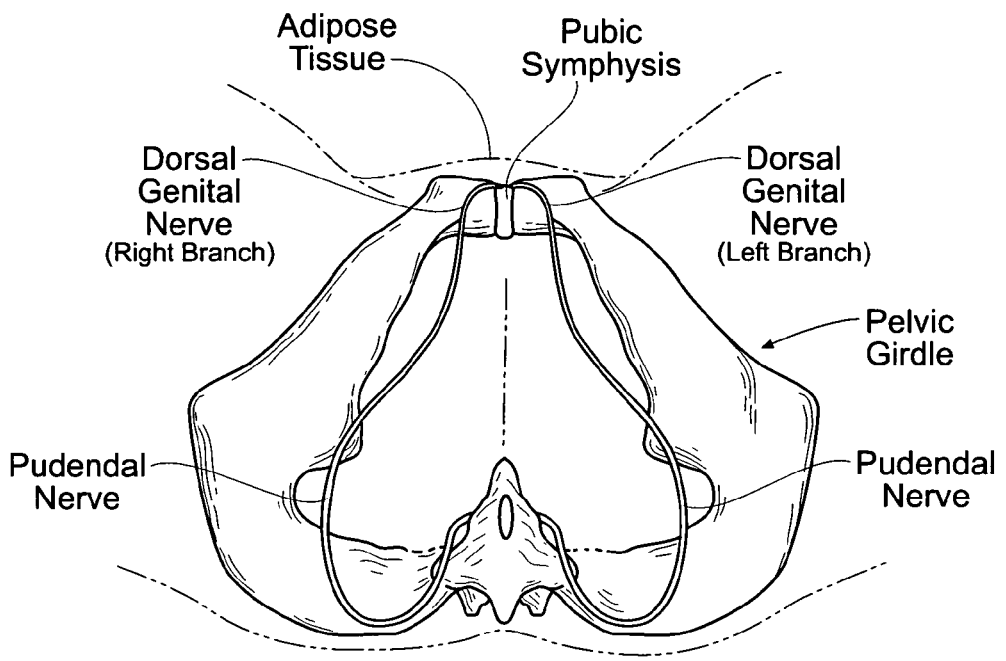
FIG. 11 is an inferior view of a female pelvic girdle region.

The Figures are largely based upon the anatomy of a male, but the parts of the male perineum are homologues of the female. As shown in FIG. 11, which is based on the anatomy of a female, the bilateral left and right branches extend anteriorly through the perineum, each ending as the dorsal genital nerve of the penis or clitoris. The genital nerves are the chief sensory nerve of the external genitalia.

As FIG. 11 shows, in the female and male, adipose tissue overlays the pubic symphysis. The bilateral branches of the genital nerves innervate this tissue region. In the female, this tissue region is known as the mons pubis. In the male, the penis and scrotum extend from this region. Further discussion regarding the fixation of the lead 12 and electrode 16 in adipose tissue will be described later.

D. Conditions Required to Evoke Erection

Erection is a complex process involving control from the autonomic and somatic nervous systems. There are two peripheral neural pathways that control erection in cats and dogs. The parasympathetic pathway (S2-S4) mediates tactile, as well as psychically induced erection, while the sympathetic pathway (T10-L2) mediates only psychically induced erection. Although erection involves many central and psychogenic factors, reflex erections are mediated by a spinal mechanism, and do not require participation of supraspinal structures.

The implant system 10 will focus on spinally-mediated reflex erection, as this is most relevant to restoration of sexual function. The afferents of the erection reflex arises from the dorsal nerve of the penis (DNP), while the efferent side includes both the cavernous and pudendal nerves (see FIG. 1). The cavernous nerve mediates engorgement of the penis as a result of dilation of penile blood vessels (mediated by a non-adrenergic non-cholinergic mechanism, putatively nitric oxide), and venous occlusion may also play a role in engorgement. The pudendal nerve carries the somatic innervation of the bulbospongiosus which serves to further increase cavernous pressure and penile stiffness, and the ischiocavernosus which can also augment stiffness of the penis.

Previous studies indicate that electrical stimulation of the dorsal nerve of the penis can evoke reflex penile erection before and after T8 spinal cord transection in the rat. In the spinalized rat, DNP stimulation produces a copulatory-like reflex, including erectile and ejaculatory responses. DNP stimulation evokes central reflexes with latencies of 50 milliseconds to 150 milliseconds and is thought to mediate reflex erection. Stimulus frequencies of two Hz to ten Hz have been successful in eliciting reflex erections before and after spinalization, and spinalization increases the combination of stimulus parameters that are successful in evoking erection.

Low amplitude genital nerve stimulation is not expected to cause pain because it has been observed that low amplitude ($5\pm3$ mA), low frequency (10 Hz) electrical stimulation of the dorsal genital (clitoral) nerve created a sensation that was well tolerated by all women (n=17), often described as a thumping (24%), buzzing (18%), or pulsing (12%) sensation, and the amplitude could be increased to almost double ($9\pm3$ mA) before it became uncomfortable.

The implant system 10 is sized and configured to evoke a rigid erection and sustain an erection for about 30 minutes that is comparable in both 1) corpus cavernous pressure (CCP) and 2) CCP/BP (blood pressure) to the erection produced by intracavernous injection of alprostadil. A rigid erection is defined by CCP$\geq$BP and a functional score of 4 or 5 (sufficient for sexual intercourse or full erection) on the Schramek grading system. The time to erection once the implant system 10 is turned on may be in the range of a few minutes (e.g., two to ten minutes). When the implant system is turned off, the erection will subside comparable to a normal healthy response.

E. Afferent and Efferent Stimulation

The system and methods described for afferent stimulation can provide a more rigid and longer lasting erection than methods that use efferent stimulation because afferent stimulation activates a reflex that coordinates the increase of filling via dilation of penile arteries with the prevention of leakage via occlusion of penile veins. Present stimulation methods do not stimulate both cavernous and pudendal nerves (or nerve branches), nor do present stimulation methods use reflexes to coordinate the individual processes involved in erection. Specifically, afferent stimulation can 1) provide a longer lasting erection because it activates a reflex that controls the rate and amount of neurotransmitter released from the cavernous nerve. On the other hand, direct efferent stimulation of the cavernous nerve can release excessive amounts of neurotransmitter. The reflex activated by afferent stimulation also 2) coordinates efferent activity in the pudendal nerve to prevent leakage of blood from the penis via occlusion of penile veins, whereas efferent stimulation of the cavernous nerve does nothing to prevent leakage of blood from the penis Additionally, efferent stimulation risks generating the perception of pain due to the current amplitude that may be required. Afferent stimulation may avoid the generation of pain because lower amplitudes of current can be used to activate selectively the large sensory fibers without activating the smaller C-fibers that transmit signals to pain centers.

Nevertheless, a coordinated stimulation to both afferent and efferent nerves, or efferent and efferent nerves, including coordinated stimulation of both the cavernous and pudendal nerves (or branches), may also be used to produce the desired functional result.

II. Details of Implant System

A. The Implantable Pulse Generator

As previously described, FIG. 6 shows a system 10 for the functional restoration of sexual function. The assembly includes an implantable lead 12 and electrode 16 coupled to an implantable pulse generator or IPG 18. The lead 12 and the implantable pulse generator 18 are shown implanted within a tissue region T of a human or animal body.

Desirably, the components of the implantable pulse generator 18 are sized and configured so that they can accommodate several different indications, without major change or modification (see FIG. 7A). Examples of components that desirably remain unchanged for different indications include the case 26, the battery 22, the microcontroller 24, much of the software (firmware) of the embedded code, the power management circuitry 40, and the stimulus power supply, both of which are part of the circuitry 20. Thus, a new indication may require only changes to the programming of the microcontroller 24. Most desirably, the particular code is remotely embedded in the microcontroller 24 after final assembly, packaging, and sterilization of the implantable pulse generator 18.

Certain components of the implantable pulse generator 18 may be expected to change as the indication changes; for example, due to differences in leads and electrodes, the connection header 14 and associated receptacle(s) for the lead may be configured differently for different indications. Other aspects of the circuit 20 may also be modified to accommodate a different indication; for example, the stimulator output stage(s), sensor(s) and/or sensor interface circuitry.

In this way, the implantable pulse generator 18 accommodates implanting in diverse tissue regions and also accommodates coupling to a lead 12 and an electrode 16 having diverse forms and configurations, again depending upon the therapeutic or functional effects desired. For this reason, the implantable pulse generator can be considered to be general purpose or "universal."

1. Desirable Technical Features

The implantable pulse generator 18 can incorporate various technical features to enhance its universality.

a. Small, Composite Case

Figure 2:
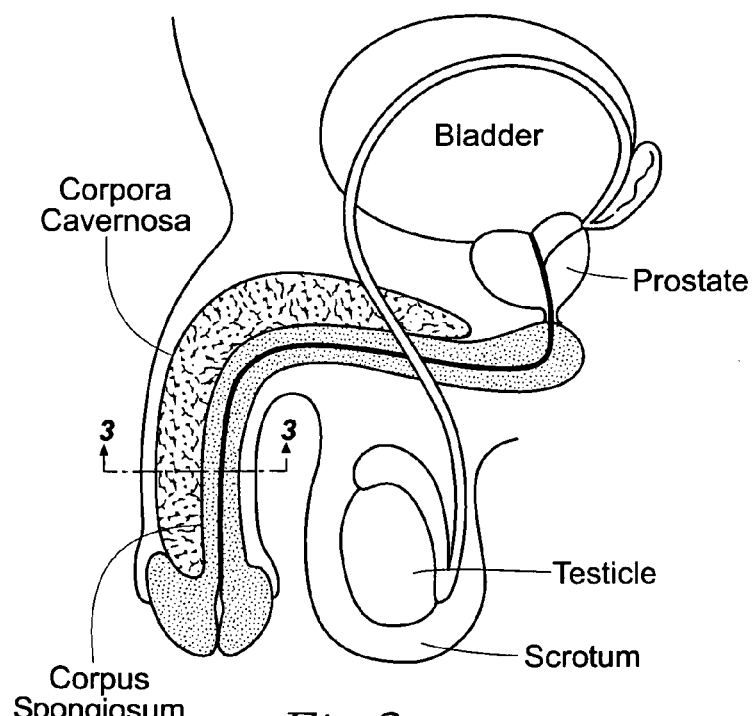
FIG. 2 is a lateral cross-sectional view of a penis, showing the relationship of the erectile tissue inside the penis.
Figure 3:
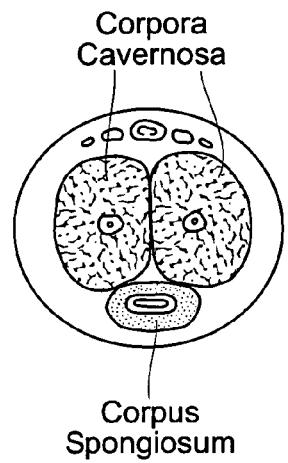
FIG. 3 is an end section view of the penis taken generally along line 3-3 of FIG. 2.
Figure 4:
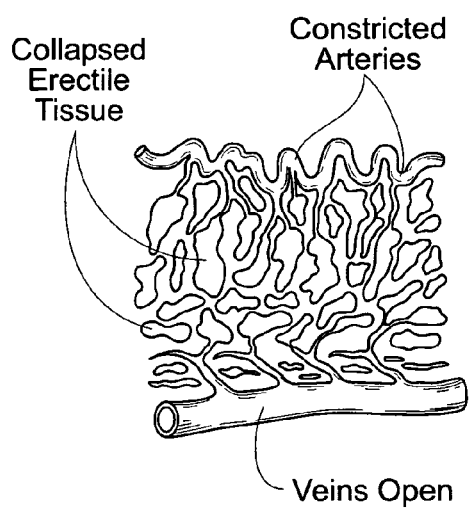
FIG. 4 is a side sectional view of penile tissue prior to an erection.
Figure 5:
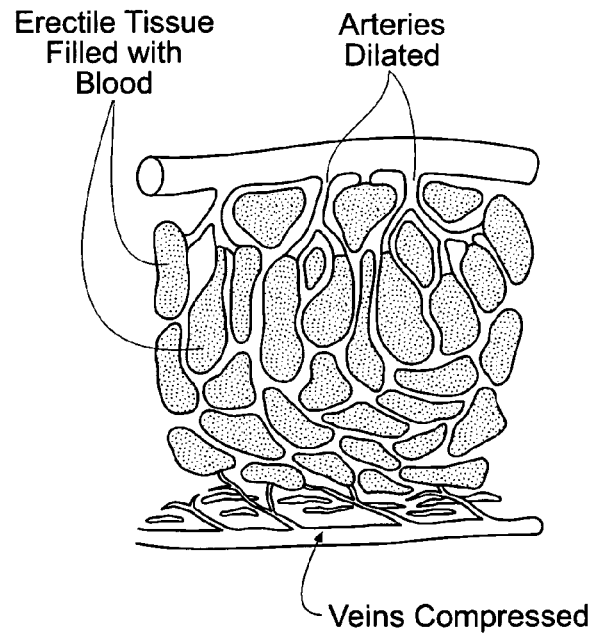
FIG. 5 is a side sectional view of penile tissue as shown in FIG. 4, showing the changes in the penile tissue causing an erection.

According to one desirable technical feature, the implantable pulse generator 18 can be sized small enough to be implanted (or replaced) with only local anesthesia. As FIGS. 7A and 7B show, the functional elements of the implantable pulse generator 18 (e.g., circuit 20, the microcontroller 24, the battery 22, and the connection header 14) are integrated into a small, composite case 26. As can be seen in FIGS. 2A and 2B, the implantable pulse generator 18 may comprise a case 26 having a small cross section, e.g., (5 mm to 15 mm thick)×(45 mm to 60 mm wide)×(45 mm to 60 mm long). The overall weight of the implantable pulse generator 18 may be approximately twenty to thirty grams. These dimensions make possible implantation of the case 26 with a small incision; i.e., suitable for minimally invasive implantation. Additionally, a smaller or larger, but similarly shaped IPG might be required for other applications, such as with more stimulus channels (thus requiring a large connection header) and/or a smaller or larger internal battery.

The case 26 of the implantable pulse generator 18 is desirably shaped with a smaller end 30 and a larger end 32. As FIG. 6 shows, this geometry allows the smaller end 30 of the case 26 to be placed into the skin pocket P first, with the larger end 32 being pushed in last.

Desirably, the case 26 for the implantable pulse generator 18 comprises a laser welded implant grade titanium material. This construction offers high reliability with a low manufacturing cost. The clam shell construction has two stamped or successively drawn titanium case halves that are laser welded around the circuit assembly and battery 22 with feed-thrus. Typically, a molded plastic spacing nest is used to hold the battery 22, the circuit 20, and perhaps a power recovery (receive) coil (if a rechargeable battery is used) together and secure them within the hermetically sealed titanium case. An implantable pulse generator having a rechargeable battery can be used of the type described in copending U.S. patent application Ser. No. 11/150,418, filed 10 Jun. 2005 and entitled "Implantable Pulse Generator for Providing Functional and/or Therapeutic Stimulation of Muscles and/or Nerves and/or Central Nervous System Tissue," which is incorporated herein by reference. The electronics may be fabricated on a flexible or flex-rigid PC board using very high density technique include adhesive flip-chip or chip-on-board mounting of the larger semiconductor devices. The tissue contact materials used in the manufacture of the IPG may all have Master Files with FDA demonstrating their biocompatibility.

The implantable pulse generator 18 shown in FIGS. 7A and 7B includes a clam-shell case 26 having a thickness that is selected to provide adequate mechanical strength The implantable pulse generator 18 may be implanted at a target implant depth of not less than five millimeters beneath the skin, and not more than fifteen millimeters beneath the skin, although this implant depth may change due to the particular application, or the implant depth may change over time based on physical conditions of the patient.

b. Primary Power Source

According to one desirable technical feature, the implantable pulse generator 18 desirably possesses an internal battery capacity sufficient to allow a service life of greater than three years with the stimulus being a high duty cycle, e.g., virtually continuous, low frequency, low current stimulus pulses, or alternatively, the stimulus being higher frequency and amplitude stimulus pulses that are used only intermittently, e.g., a very low duty cycle.

To achieve this feature, the primary battery 22 of the implantable pulse generator 18 desirably comprises a primary power source; most desirably an implant grade Lithium Ion battery 22. Given the average quiescent operating current (estimated at 8 μA plus 35 μA for a wireless telemetry receiver pulsing on twice every second) and a seventy percent efficiency of the stimulus power supply, a 1.0 Amp-hr primary cell battery can provide a service life of less than two years, which is too short to be clinically or commercially viable for this indication. Therefore, the implantable pulse generator 18 desirably incorporates a primary battery, e.g., a Lithium Ion battery. Given representative desirable stimulation parameters (which will be described later), a Lithium Ion battery with a capacity of at least 30 mA-hr will operate for over three years. Lithium Ion implant grade batteries are available from a domestic supplier. A representative battery provides 35 mA-hr in a package configuration that is of appropriate size and shape to fit within the implantable pulse generator 18.

The implantable pulse generator 18 desirably incorporates circuitry and/or programming to assure that the implantable pulse generator 18 will suspend stimulation, and perhaps fall-back to only very low rate telemetry, and eventually suspends all operations when the primary battery 22 has discharged the majority of its capacity (i.e., only a safety margin charge remains) Once in this dormant mode, the implantable pulse generator may provide limited communications and is in condition for replacement.

c. Wireless Telemetry

According to one desirable technical feature, the system or assembly 10 includes an implantable pulse generator 18, which desirably incorporates wireless telemetry (rather that an inductively coupled telemetry) for a variety of functions to be performed within arm's reach of the patient, the functions including receipt of programming and clinical parameters and settings from the clinician programmer 36, communicating usage history to the clinician programmer, and providing user control of the implantable pulse generator 18. Each implantable pulse generator may also have a unique signature that limits communication to only the dedicated controllers (e.g., the matched patient controller, or a clinician programmer configured for the implantable pulse generator in question).

Figure 15:
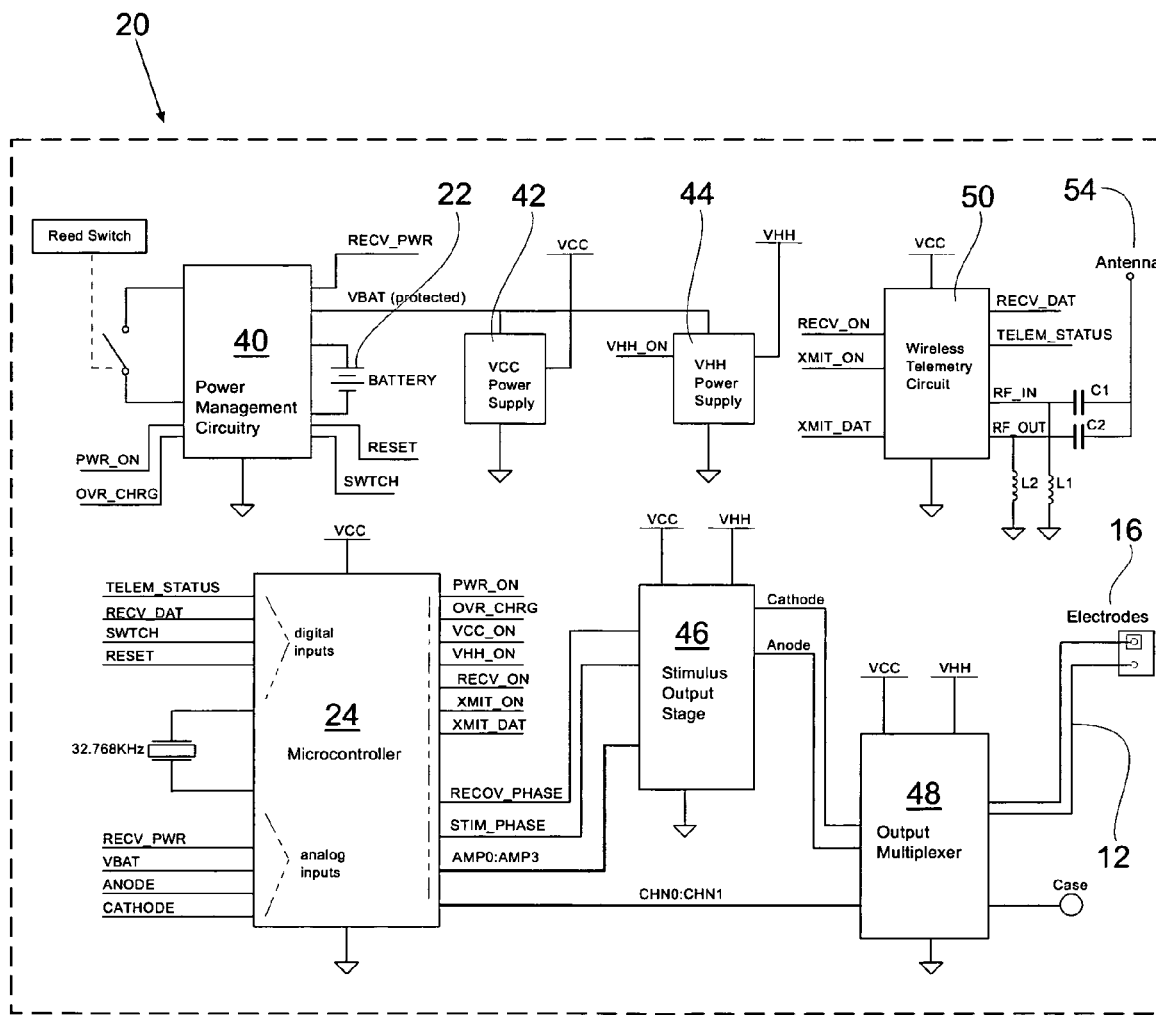
FIG. 15 is a block diagram of a circuit that the implantable pulse generator shown in FIGS. 7A and 7B can incorporate.
Figure 16:
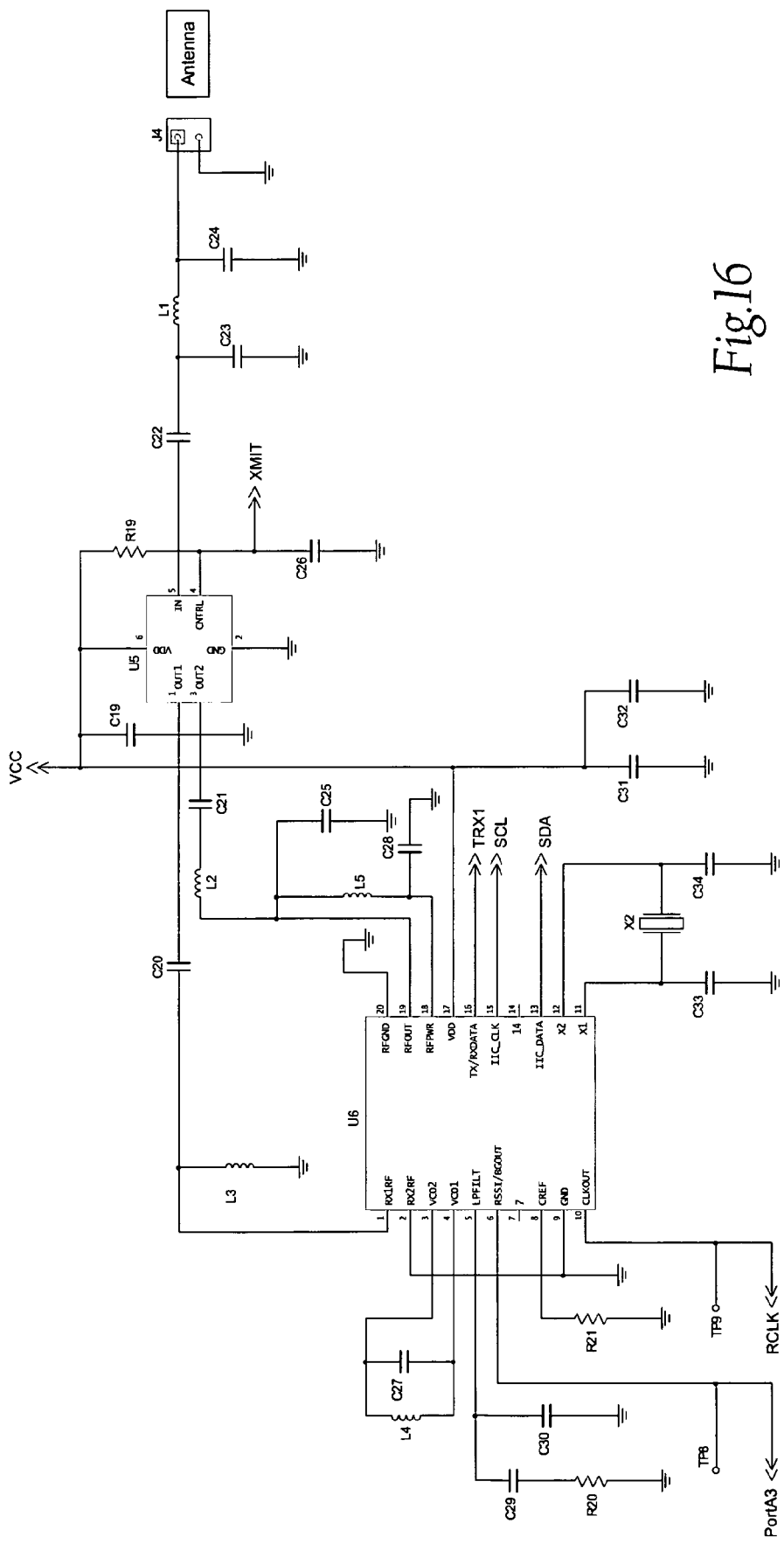
FIG. 16 is a circuit diagram showing a possible circuit for the wireless telemetry feature used with the implantable pulse generator shown in FIGS. 7A and 7B.

The implantable pulse generator 18 desirably incorporates wireless telemetry as an element of the implantable pulse generator circuit 20 shown in FIG. 15. A circuit diagram showing a desired configuration for the wireless telemetry feature is shown in FIG. 16. It is to be appreciated that modifications to this circuit diagram configuration which produce the same or similar functions as described are within the scope of the invention.

Figure 12:
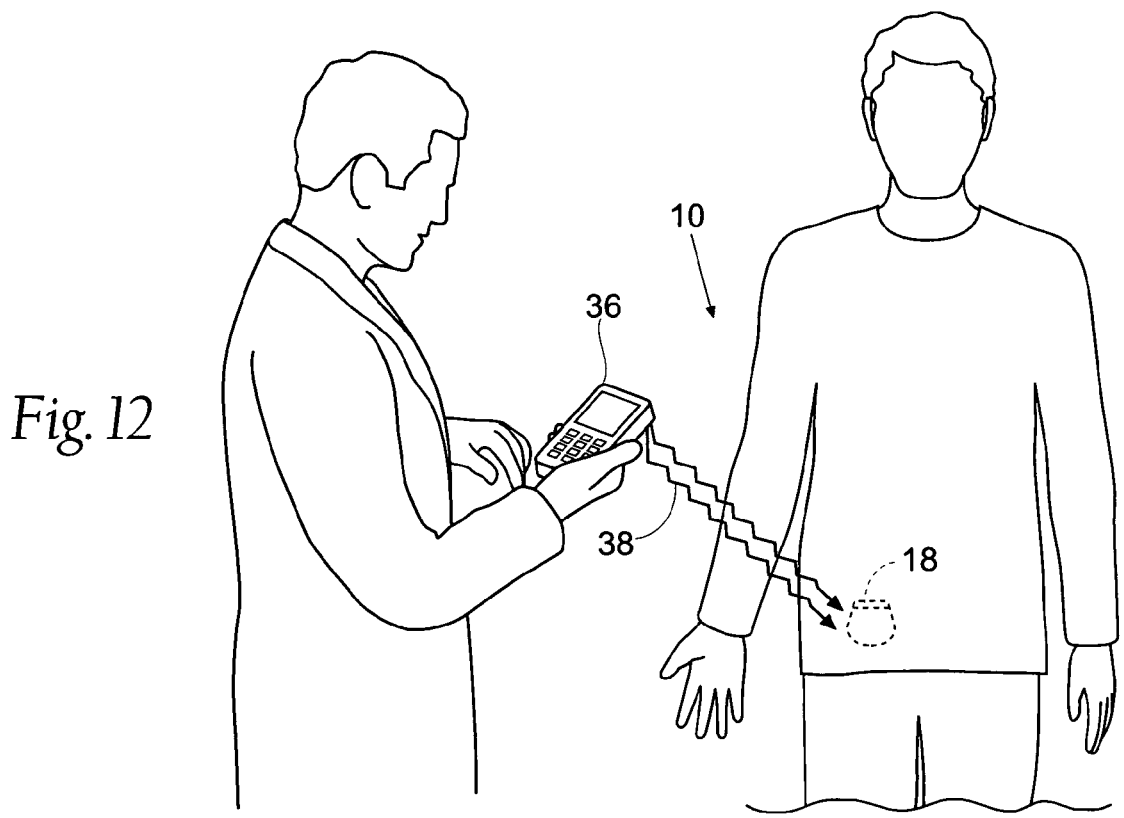
FIG. 12 is an anatomic view showing the implantable pulse generator shown in FIGS. 7A and 7B in association with an external programmer that relies upon wireless telemetry, and showing the programmer's capability of communicating with the implantable pulse generator up to an arm's length away from the implantable pulse generator.

As shown in FIG. 12, the assembly 10 desirably includes a clinician programmer 36 that, through a wireless telemetry 38, transfers commands, data, and programs into the implantable pulse generator 18 and retrieves data out of the implantable pulse generator 18. In some configurations, the clinician programmer may communicate with more than one implantable pulse generator implanted in the same user.

Figure 13:
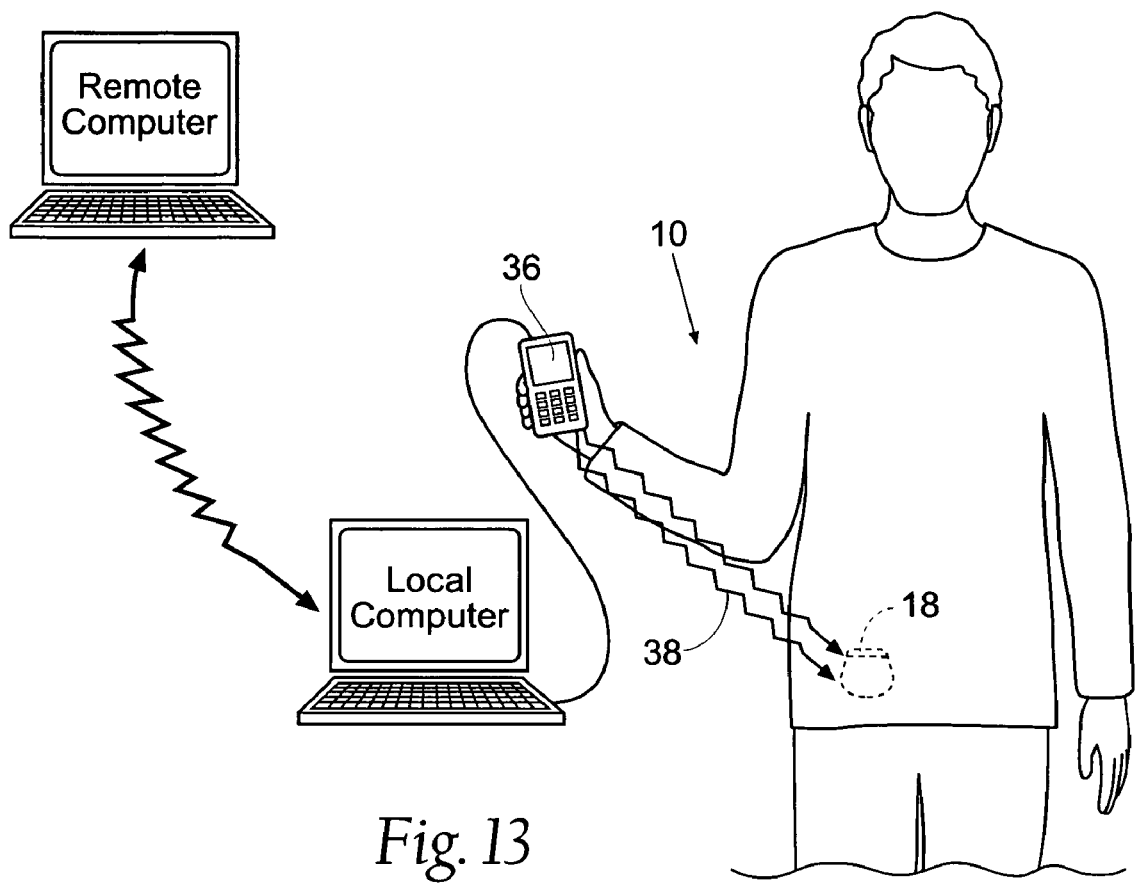
FIG. 13 is a system view of an implantable pulse generator system incorporating a clinician programmer derivative and showing the system's capability of communicating and transferring data over a network, including a remote network.

The clinician programmer 36 may incorporate a custom programmed general purpose digital device., e.g., a custom program, industry standard handheld computing platform or other personal digital assistant (PDA). The clinician programmer 36 can include an on-board microcontroller powered by a rechargeable battery. The rechargeable battery of the clinician programmer 36 may be recharged by being docked on a charging base (not shown); or the custom electronics of the clinician programmer may receive power from the connected PDA. The microcontroller carries embedded code which may include pre-programmed rules or algorithms that allow a clinician to remotely download program stimulus parameters and stimulus sequences parameters into the implantable pulse generator 18. The microcontroller of the clinician programmer 36 is also desirably able to interrogate the implantable pulse generator and upload usage data from the implantable pulse generator. FIG. 12 shows one possible application where the clinician is using the programmer 36 to interrogate the implantable pulse generator. FIG. 13 shows an alternative application where the clinician programmer, or a clinician programmer derivative 33 intended for remote programming applications and having the same or similar functionality as the clinician programmer, is used to interrogate the implantable pulse generator. As can be seen, the clinician programmer derivative 33 is connected to a local computer, allowing for remote interrogation via a local area network, wide area network, or Internet connection, for example.

Using subsets of the clinician programmer software, features of the clinician programmer 36 or clinician programmer derivative 33 might include the ability of the clinician or physician to remotely monitor and adjust parameters using the Internet or other known or future developed networking schemes. A clinician programmer derivative 33 would desirably connect to the patient's computer in their home through an industry standard network such as the Universal Serial Bus (USB), where in turn an applet downloaded from the clinician's server would contain the necessary code to establish a reliable transport level connection between the implantable pulse generator 18 and the clinician's client software, using the clinician programmer derivative 33 as a bridge. Such a connection may also be established through separately installed software. The clinician or physician could then view relevant diagnostic information, such as the health of the unit or its current settings, and then modify the stimulus settings in the IPG or direct the patient to take the appropriate action. Such a feature would save the clinician, the patient and the health care system substantial time and money by reducing the number of office visits during the life of the implant.

Other features of the clinician programmer, based on an industry standard platform, might include the ability to connect to the clinician's computer system in his or hers office. Such features may take advantage of the Conduit connection employed by Palm OS based devices. Such a connection then would transfer relevant patient data to the host computer or server for electronic processing and archiving. With a feature as described here, the clinician programmer then becomes an integral link in an electronic chain that provides better patient service by reducing the amount of paperwork that the physician's office needs to process on each office visit. It also improves the reliability of the service since it reduces the chance of mis-entered or mis-placed information, such as the record of the parameter setting adjusted during the visit.

With the use of a patient controller 37 (see FIG. 14), the wireless link 38 allows a patient to control certain parameters of the implantable pulse generator within a predefined limited range. The parameters may include the operating modes/states, increasing/decreasing or optimizing stimulus patterns, or providing open or closed loop feedback from an external sensor or control source. The wireless telemetry 38 also desirably allows the user to interrogate the implantable pulse generator 18 as to the status of its internal battery 22. The full ranges within these parameters may be controlled, adjusted, and limited by a clinician, so the user may not be allowed the full range of possible adjustments.

In one embodiment, the patient controller 37 is sized and configured to couple to a key chain, as seen in FIG. 14. It is to be appreciated that the patient controller 37 may take on any convenient shape, such as a ring on a finger, or a watch on a wrist, or an attachment to a belt, for example. The patient controller may also use a magnetic switch to enable the user to turn the IPG on/off.

The wireless telemetry may incorporate a suitable, low power wireless telemetry transceiver (radio) chip set that can operate in the MICS (Medical Implant Communications Service) band (402 MHz to 405 MHz) or other VHF/UHF low power, unlicensed bands. A wireless telemetry link not only makes the task of communicating with the implantable pulse generator 18 easier, but it also makes the link suitable for use in motor control applications where the user issues a command to the implantable pulse generator to produce muscle contractions to achieve a functional goal (e.g., to stimulate ankle flexion to aid in the gait of an individual after a stroke) without requiring a coil or other component taped or placed on the skin over the implanted implantable pulse generator.

Appropriate use of power management techniques is important to the effective use of wireless telemetry. Desirably, the implantable pulse generator is exclusively the communications slave, with all communications initiated by the external controller (the communications master). The receiver chip of the implantable pulse generator is OFF more than 99% of the time and is pulsed on periodically to search for a command from an external controller, including but not limited to the clinician programmer 36 and the patient controller 37. Communications protocols include appropriate check and message acknowledgment handshaking to assure the necessary accuracy and completeness of every message. Some operations (such as reprogramming or changing stimulus parameters) require rigorous message accuracy testing and acknowledgement. Other operations, such as a single user command value in a string of many consecutive values, might require less rigorous checking and a more loosely coupled acknowledgement.

The timing with which the implantable pulse generator enables its transceiver to search for RF telemetry from an external controller is precisely controlled (using a time base established by a quartz crystal) at a relatively low rate, e.g., the implantable pulse generator may look for commands from the external controller at a rate of less than one (1) Hz. This equates to a monitoring interval of several seconds. It is to be appreciated that the monitoring rate may vary faster or slower depending on the application, (e.g., twice per second; i.e., every 500 milliseconds). This allows the external controller to time when the implantable pulse generator responds to a command and then to synchronize its commands with when the implantable pulse generator will be listening for commands. This, in turn, allows commands issued within a short time (seconds to minutes) of the last command to be captured and acted upon without having to 'broadcast' an idle or pause signal for 500 milliseconds before actually issuing the command in order to know that the implantable pulse generator will have enabled its receiver and received the command. Similarly, the communications sequence is configured to have the external controller issue commands in synchronization with when the implantable pulse generator will be listening for a command. Similarly, the command set implemented is selected to minimize the number of messages necessary and the length of each message consistent with the appropriate level of error detection and message integrity monitoring. It is to be appreciated that the monitoring rate may vary faster or slower depending on the application; and may vary over time within a given application.

A suitable radio chip is used for the half duplex wireless communications, e.g., the AMIS-52100 (AMI Semiconductor; Pocatello, Id.). This transceiver chip is designed specifically for the MICS and its European counter-part the ULP-AMI (Ultra Low Power-Active Medical Implant) band. This chip set is optimized by micro-power operation with rapid start-up, and RF 'sniffing' circuitry.

d. Stimulus Output Stage

According to one desirable technical feature, the implantable pulse generator 18 desirably uses a single stimulus output stage (generator) that is directed to one or more output channels (electrode surfaces) by analog switch(es) or analog multiplexer(s). Desirably, the implantable pulse generator 18 will deliver at least one channel of stimulation via a lead/electrode. For applications requiring more stimulus channels, several channels (perhaps up to four) can be generated by a single output stage. In turn, two or more output stages could be used, each with separate multiplexing to multiple channels, to allow an implantable pulse generator with eight or more stimulus channels. The stimulation waveform output of the IPG desirably has an asymmetrically biphasic waveform (net DC current less than 10 µA), and an RC recovery phase with programmable interphase delay. The stimulus parameters (amplitude, pulse duration, and frequency) are independently adjustable with amplitude output ranging from 0.5 mA to 20 mA, pulse duration ranging from 0 to 500 microseconds, and frequency ranging from 1 (one) to 300 Hz. In one embodiment, the applied stimulus frequency may be in the range of about one Hz to about fifteen Hz. The stimulus current (amplitude) and pulse duration being programmable on a channel to channel basis and adjustable over time based on a clinically programmed sequence or regime or based on user (patient) commands received via the wireless communications link.

Figure 17:
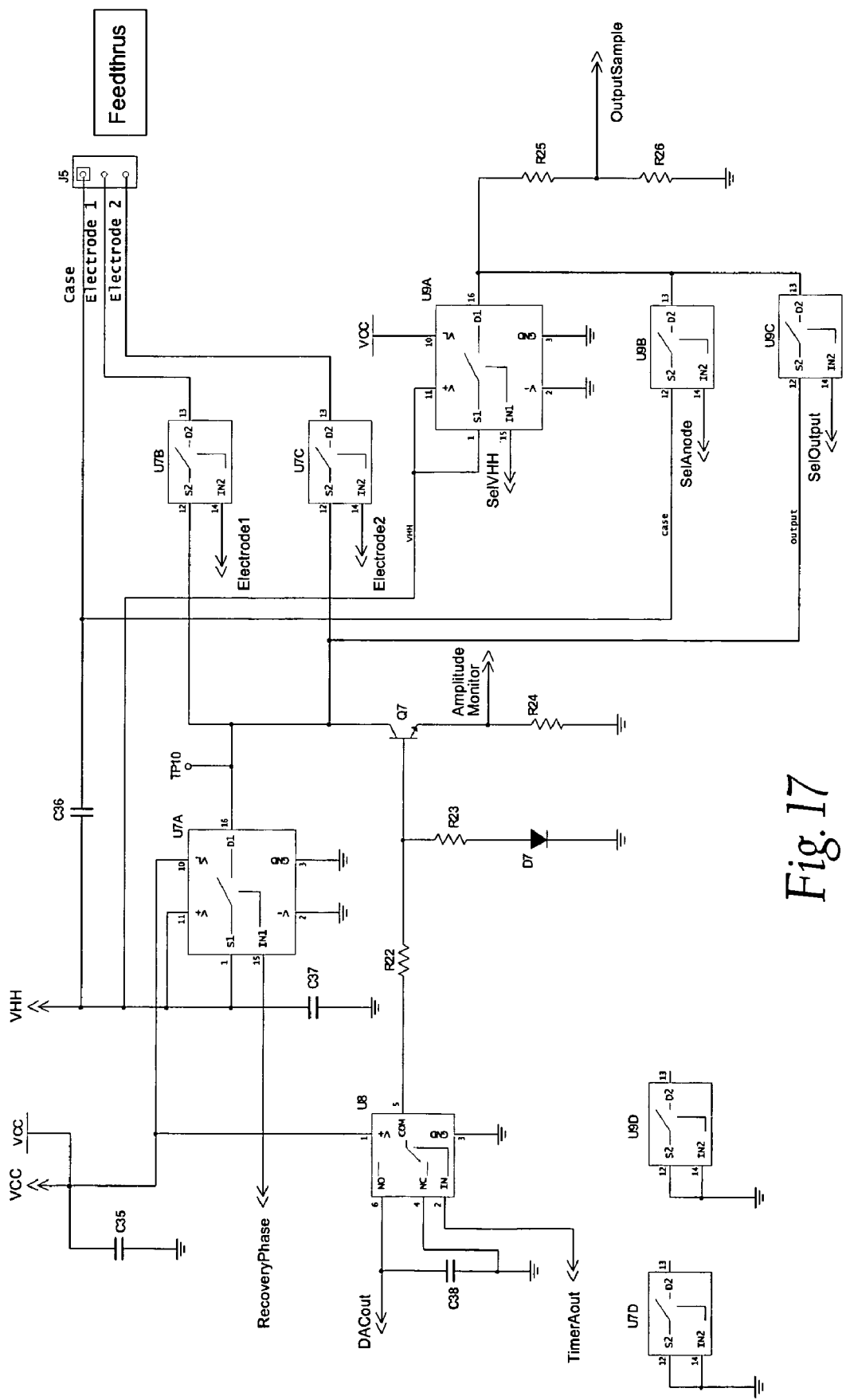
FIG. 17 is a circuit diagram showing a possible circuit for the stimulus output stage and output multiplexing features used with the implantable pulse generator shown in FIGS. 7A and 7B.

A circuit diagram showing a desired configuration for the stimulus output stage feature is shown in FIG. 17. It is to be appreciated that modifications to this circuit diagram configuration which produce the same or similar functions as described are within the scope of the invention.

Figure 18:
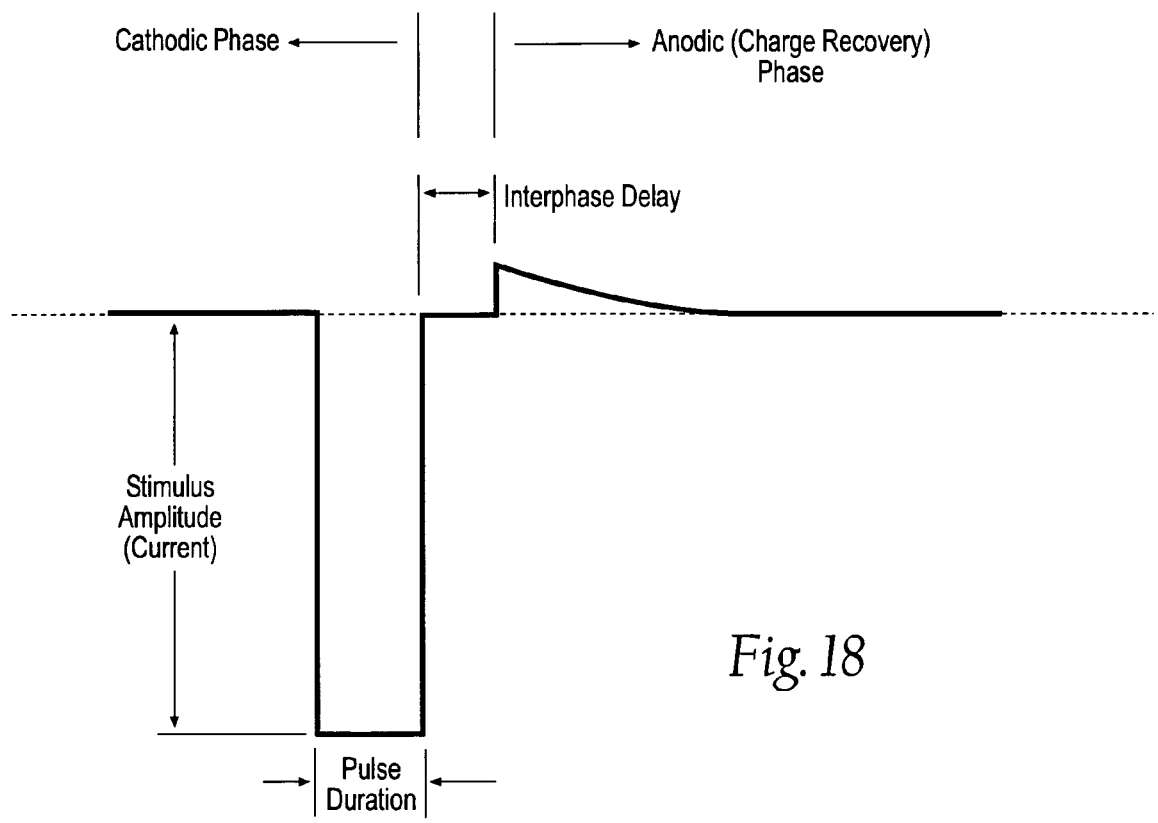
FIG. 18 is a graphical view of a desirable biphasic stimulus pulse output of the implantable pulse generator for use with the system shown in FIG. 6.

Desirably, the implantable pulse generator 18 includes a single stimulus generator (with its associated DC current blocking output capacitor) which is multiplexed to a number of output channels; or a small number of such stimulus generators each being multiplexed to a number of output channels. This circuit architecture allows multiple output channels with very little additional circuitry. A typical, biphasic stimulus pulse is shown in FIG. 18. Note that the stimulus output stage circuitry 46 may incorporate a mechanism to limit the recovery phase current to a small value (perhaps 0.5 mA). Also note that the stimulus generator (and the associated timing of control signals generated by the microcontroller) may provide a delay (typically of the order of 100 microseconds) between the cathodic phase and the recovery phase to limit the recovery phase diminution of the cathodic phase effective at eliciting a neural excitation. The charge recovery phase for any electrode (cathode) must be long enough to assure that all of the charge delivered in the cathodic phase has been returned in the recovery phase; i.e., greater than or equal to five time constants are allowed for the recovery phase. This will allow the stimulus stage to be used for the next electrode while assuring there is no net DC current transfer to any electrode. Thus, the single stimulus generator having this characteristic would be limited to four channels (electrodes), each with a maximum frequency of 30 Hz to 50 Hz. This operating frequency exceeds the needs of many indications for which the implantable pulse generator is well suited. For applications requiring more channels (or higher composite operating frequencies), two or more separate output stages might each be multiplexed to multiple (e.g., four) electrodes.

e. The Lead Connection Header

According to one desirable technical feature, the implantable pulse generator 18 desirably includes a lead connection header 14 for connecting the lead(s) 12 that will enable reliable and easy replacement of the lead/electrode (see FIGS. 7A and 7B), and includes a small antenna 54 for use with the wireless telemetry feature.

The implantable pulse generator desirably incorporates a connection header (top header) 14 that is easy to use, reliable, and robust enough to allow multiple replacements of the implantable pulse generator after many years (e.g., more than ten years) of use. The surgical complexity of replacing an implantable pulse generator is usually low compared to the surgical complexity of correctly placing the implantable lead 12/electrode 16 in proximity to the target nerve/tissue and routing the lead 12 to the implantable pulse generator. Accordingly, the lead 12 and electrode 16 desirably has a service life of at least ten years with a probable service life of fifteen years or more. Based on the clinical application, the implantable pulse generator may not have this long a service life. The implantable pulse generator service life is largely determined by the power capacity of the Lithium Ion battery 22, and is likely to be three to ten years, based on the usage of the device. Desirably, the implantable pulse generator 18 has a service life of at least three years.

As described above, the implantable pulse generator preferably will use a laser welded titanium case. As with other active implantable medical devices using this construction, the implantable lead(s) 12 connect to the implantable pulse generator through a molded or cast polymeric connection header 14 (top header). Metal-ceramic or metal-glass feed-thrus maintain the hermetic seal of the titanium capsule while providing electrical contact to the electrical contacts of the lead 12/electrode 16.

The standard implantable connectors may be similar in design and construction to the low-profile IS-1 connector system (per ISO 5841-3). The IS-1 connectors have been in use since the late 1980s and have been shown to be reliable and provide easy release and re-connection over several implantable pulse generator replacements during the service life of a single pacing lead. Full compatibility with the IS-1 standard, and mating with pacemaker leads, is not a requirement for the implantable pulse generator.

The implantable pulse generator connection system may include a modification of the IS-1 connector system, which shrinks the axial length dimensions while keeping the format and radial dimensions of the IS-1. For application with more than two electrode conductors, the top header 14 may incorporate one or more connection receptacles each of which accommodate leads with typically four conductors. When two or more leads are accommodated by the header, these leads may exit the connection header in opposite directions (i.e., from opposite sides of the header).

These connectors can be similar to the banded axial connectors used by other multi-polar implantable pulse generators or may follow the guidance of the draft IS-4 implantable connector standard. The design of the implantable pulse generator housing and header 14 preferably includes provisions for adding the additional feed-thrus and larger headers for such indications.

The inclusion of the UHF antenna 54 for the wireless telemetry inside the connection header (top header) 14 is necessary as the shielding offered by the titanium case will severely limit (effectively eliminate) radio wave propagation through the case. The antenna 54 connection will be made through a feed-thru similar to that used for the electrode connections. Alternatively, the wireless telemetry signal may be coupled inside the implantable pulse generator onto a stimulus output channel and coupled to the antenna 54 with passive filtering/coupling elements/methods in the connection header 14.

f. The Microcontroller

According to one desirable technical feature, the implantable pulse generator 18 desirably uses a standard, commercially available micro-power, flash programmable microcontroller 24 or processor core in an application specific integrated circuit (ASIC). This device (or possibly more than one such device for a computationally complex application with sensor input processing) and other large semiconductor components may have custom packaging such as chip-on-board, solder flip chip, or adhesive flip chip to reduce circuit board real estate needs.

Figure 19:
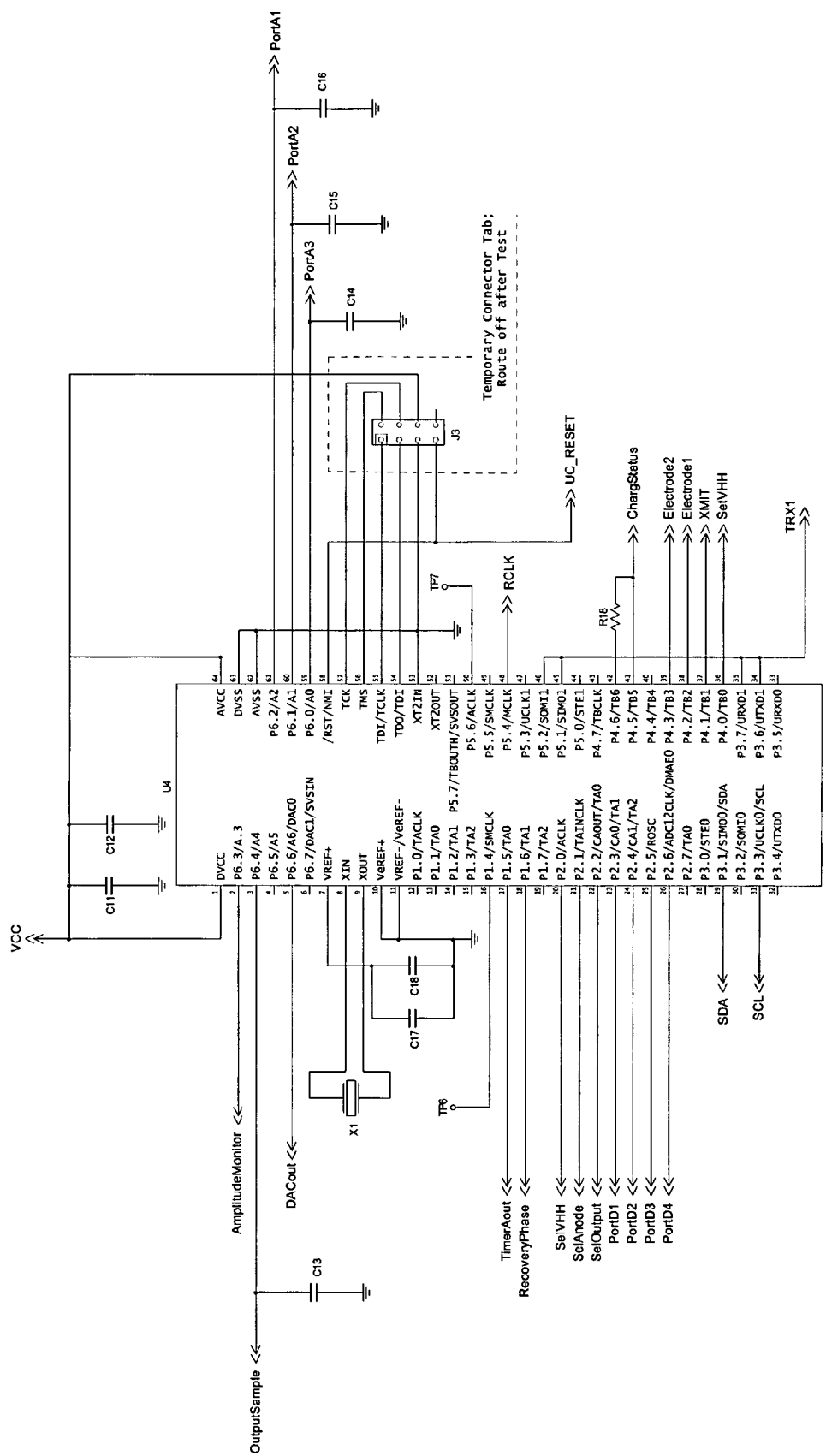
FIG. 19 is a circuit diagram showing a possible circuit for the microcontroller used with the implantable pulse generator shown in FIGS. 7A and 7B.

A circuit diagram showing a desired configuration for the microcontroller 24 is shown in FIG. 19. It is to be appreciated that modifications to this circuit diagram configuration which produce the same or similar functions as described are within the scope of the invention.

g. Power Management Circuitry

Figure 20:
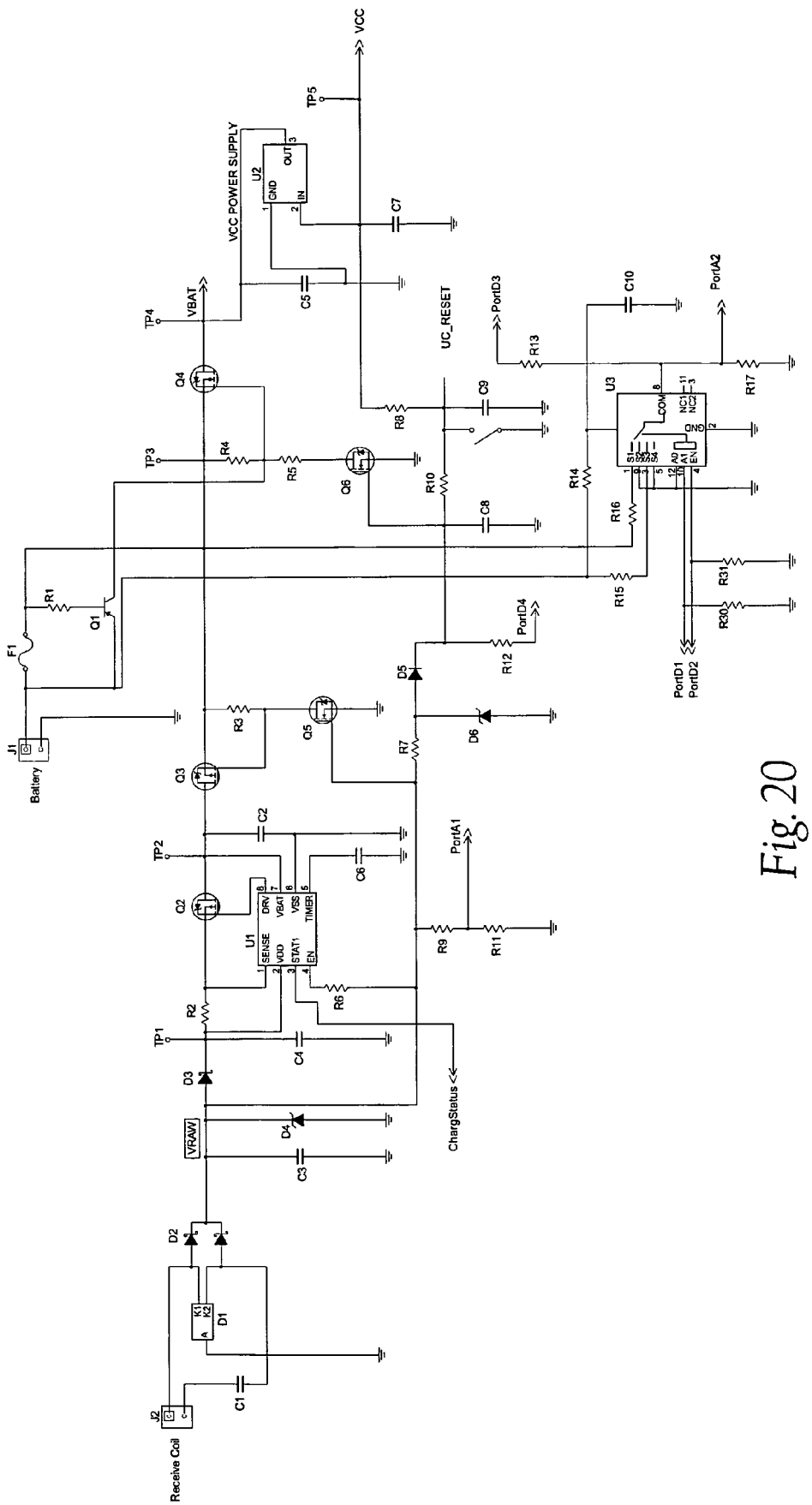
FIG. 20 is a circuit diagram showing one possible option for a power management sub-circuit where the sub-circuit includes MOSFET isolation between the battery and charger circuit (when used), the power management sub-circuit being a part of the implantable pulse generator circuit shown in FIG. 6.
Figure 21:
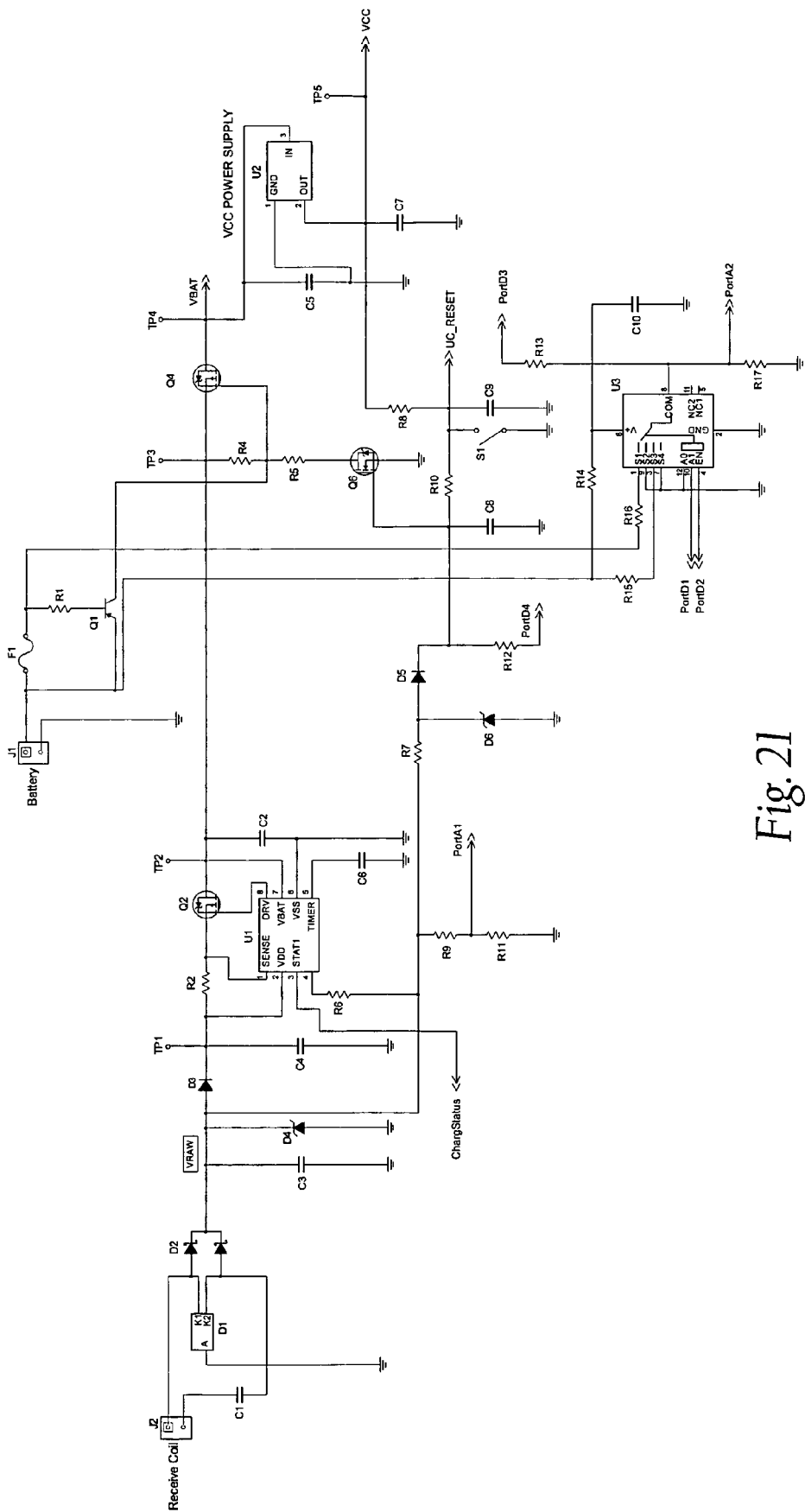
FIG. 21 is a circuit diagram showing a second possible option for a power management sub-circuit where the sub-circuit does not include MOSFET isolation between the battery and charger circuit (when used), the power management sub-circuit being a part of the implantable pulse generator circuit shown in FIG. 6.

According to one desirable technical feature, the implantable pulse generator 18 desirably includes efficient power management circuitry as an element of the implantable pulse generator circuitry 20 shown in FIG. 15. The power management circuitry is generally responsible for the efficient distribution of power and monitoring the battery 22. In addition, the operation of the implantable pulse generator 18 can be described in terms of having operating modes as relating to the function of the power management circuitry. These modes may include, but are not limited to IPG Active and IPG Dormant. These modes will be described below in terms of the principles of operation of the power management circuitry using possible circuit diagrams shown in FIGS. 20 and 21. FIG. 20 shows one possible power management sub-circuit having MOSFET isolation between the battery 22 and a charger circuit (when used). FIG. 21 shows another possible power management sub-circuit diagram without having MOSFET isolation between the battery 22 and the charger circuit (when used). In the circuit without the isolation MOSFET (see FIG. 21), the leakage current of the disabled charge control integrated circuit chip (U1) must be very low to prevent this leakage current from discharging the battery 22 in all modes (including the Dormant Mode). Except as noted, the description of these modes applies to both circuits.

i. IPG Active Mode

The IPG Active mode occurs when the implantable pulse generator 18 is operating normally. In this mode, the implantable pulse generator may be generating stimulus outputs or it may be waiting for the next request to generate stimulus in response to a timed neuromodulation sequence or a telemetry command from an external controller. In this mode, the implantable pulse generator is active (microcontroller 24 is powered and coordinating wireless communications and may be timing & controlling the generation and delivery of stimulus pulses).

i (a). Principles of Operation, IPG Active Mode

In the IPG Active mode, as can be seen in FIG. 20, the lack of DC current from VRAW means that Q5 is held off. This, in turn, holds Q3 off and a portion of the power management circuitry is isolated from the battery 22. In FIG. 21, the lack of DC current from VRAW means that U1 is disabled. This, in turn, keeps the current drain from the battery 22 to an acceptably low level, typically less than 1 µA.

ii. IPG Dormant Mode

The IPG Dormant mode occurs when the implantable pulse generator 18 is completely disabled (powered down). In this mode, power is not being supplied to the microcontroller 24 or other enabled circuitry. This is the mode for the long-term storage of the implantable pulse generator before or after implantation. The Dormant mode may only be exited by placing a pacemaker magnet (or comparable device) over the implantable pulse generator 18 for a predetermined amount of time, e.g., five seconds.

ii (a). Principles of Operation, IPG Dormant Mode

In the IPG Dormant mode, VBAT is not delivered to the remainder of the implantable pulse generator circuitry because Q4 is turned off. The Dormant mode is stable because the lack of VBAT means that VCC is also not present, and thus Q6 is not held on through R8 and R10. Thus the battery 22 is completely isolated from all load circuitry (the VCC power supply and the VHH power supply).

The Dormant mode is entered through the application of a long magnet placement over S1 (magnetic reed switch) or through the reception of a command by the wireless telemetry. In the case of the telemetry command, the PortD4, which is normally configured as a microcontroller input, is configured as a logic output with a logic low (0) value. This, in turn, discharges C8 through R12 and turns off Q6; which, in turn, turns off Q4 and forces the implantable pulse generator into the Dormant mode. Note that R12 is much smaller in value than R10, thus the microcontroller 24 can force C8 to discharge even though VCC is still present.

In FIG. 20, the lack of DC current from VRAW means that Q5 is held off. This, in turn, holds Q3 off and a portion of the power management circuitry is isolated from the battery 22. Also, Q4 was turned off. In FIG. 21, the lack of DC current from VRAW means that U1 is disabled. This, in turn, keeps the current drain from the battery 22 to an acceptably low level, typically less than 1 µA.

2. Representative Implantable Pulse Generator Circuitry

FIG. 15 shows an embodiment of a block diagram circuit 20 for the primary cell implantable pulse generator 18 that takes into account the desirable technical features discussed above. The circuit 20 can be grouped into functional blocks, which generally correspond to the association and interconnection of the electronic components.

In FIG. 15, seven functional blocks are shown: (1) The Microprocessor or Microcontroller 24; (2) the Power Management Circuit 40; (3) the VCC Power Supply 42; (4) the VHH Power Supply 44; (5) the Stimulus Output Stage(s) 46; (6) the Output Multiplexer(s) 48; and (7) the Wireless Telemetry Circuit 50.

For each of these blocks, the associated functions, possible key components, and circuit description are now described.

a. The Microcontroller

The Microcontroller 24 is responsible for the following functions:

(1) The timing and sequencing of the stimulator stage and the VHH power supply used by the stimulator stage, (2) The sequencing and timing of power management functions, (3) The monitoring of the battery voltage, the stimulator voltages produced during the generation of stimulus pulses, and the total circuit current consumption, VHH, and VCC, (4) The timing, control, and interpretation of commands to and from the wireless telemetry circuit, (5) The logging (recording) of patient usage data as well as clinician programmed stimulus parameters and configuration data, and (6) The processing of commands (data) received from the user (patient) via the wireless link to modify the characteristics of the stimulus being delivered.

The use of a microcontroller incorporating flash programmable memory allows the operating program of the implantable pulse generator as well as the stimulus parameters and settings to be stored in non-volatile memory (data remains safely stored even if the battery 22 becomes fully discharged; or if the implantable pulse generator is placed in the Dormant mode). Yet, the data (operating program, stimulus parameters, usage history log, etc.) can be erased and reprogrammed thousands of times during the life of the implantable pulse generator. The software (firmware) of the implantable pulse generator must be segmented to support the operation of the wireless telemetry routines while the flash memory of the microcontroller 24 is being erased and reprogrammed. Similarly, the VCC power supply 42 must support the power requirements of the microcontroller 24 during the flash memory erase and program operations.

Although the microcontroller 24 may be a single component, the firmware is developed as a number of separate modules that deal with specific needs and hardware peripherals. The functions and routines of these software modules are executed sequentially; but the execution of these modules are timed and coordinated so as to effectively function simultaneously. The microcontroller operations that are associated directly with a given hardware functional block are described with that block.

The Components of the Microcontroller Circuit may include:

(1) A single chip microcontroller 24. This component may be a member of the Texas Instruments MSP430 family of flash programmable, micro-power, highly integrated mixed signal microcontroller. Likely family members to be used include the MSP430F1610, MSP430F1611, MSP430F1612, MSP430F168, and the MSP430F169. Each of these parts has numerous internal peripherals, and a micropower internal organization that allows unused peripherals to be configured by minimal power dissipation, and an instruction set that supports bursts of operation separated by intervals of sleep where the microcontroller suspends most functions.

(2) A miniature, quartz crystal (X1) for establishing precise timing of the microcontroller. This may be a 32.768 KHz quartz crystal.

(3) Miscellaneous power decoupling and analog signal filtering capacitors.

b. Power Management Circuit

The Power Management Circuit 40 (including associated microcontroller actions) is responsible for the following functions:

(1) monitor the battery voltage, (2) suspend stimulation when the battery voltage becomes very low, and/or suspend all operation (go into the Dormant mode) when the battery voltage becomes critically low, (3) communicate (through the wireless telemetry link 38) with the external equipment the charge status of the battery 22, (4) prevent (with single fault tolerance) the delivery of excessive current from the battery 22, (5) provide battery power to the rest of the circuitry of the implantable pulse generator, i.e., VCC and VHH power supplies, (6) provide isolation of the Lithium Ion battery 22 from other circuitry while in the Dormant mode, (7) provide a hard microprocessor reset and force entry into the Dormant mode in the presence of a pacemaker magnet (or comparable device), and (8) provide the microcontroller 24 with analog voltages with which to measure the magnitude of the battery voltage and the appropriate battery current flow (drain and charge).

The Components of the Power Management Circuit may include:

(1) Low on resistance, low threshold P channel MOSFETs with very low off state leakage current (Q2, Q3, and Q4).

(2) Analog switches (or an analog multiplexer) U3.

(3) Logic translation N-channel MOSFETs (Q5 & Q6) with very low off state leakage current.

c. The VCC Power Supply

The VCC Power Supply 42 is generally responsible for the following functions:

(1) Some of the time, the VCC power supply passes the battery voltage to the circuitry powered by VCC, such as the microcontroller 24, stimulator output stage 46, wireless telemetry circuitry 50, etc.

(2) At other times, the VCC power supply fractionally steps up the voltage to about 3.3V; (other useable voltages include 3.0V, 2.7V, etc.) despite changes in the Lithium Ion battery 22 voltage. This higher voltage is required for some operations such as programming or erasing the flash memory in the microcontroller 24, (i.e., in circuit programming).

The voltage converter/switch part at the center of the VCC power supply may be a charge pump DC to DC converter. Typical choices for this part may include the Maxim MAX1759, the Texas Instruments TPS60204, or the Texas Instruments REG710, among others.

The characteristics of the VCC Power Supply might include:

(1) high efficiency and low quiescent current, i.e., the current wasted by the power supply in its normal operation. This value should be less than a few microamperes; and (2) drop-out voltage, i.e., the minimal difference between the VBAT supplied to the VCC power supply and its output voltage. This voltage may be less than about 100 mV even at the current loads presented by the transmitter of the wireless telemetry circuitry 50.

(3) The VCC power supply 42 may allows in-circuit reprogramming of the implantable pulse generator firmware, or optionally, the implantable pulse generator 18 may not use a VCC power supply, which may not allow in-circuit reprogramming of the implantable pulse generator firmware.

d. VHH Power Supply

Figure 22:
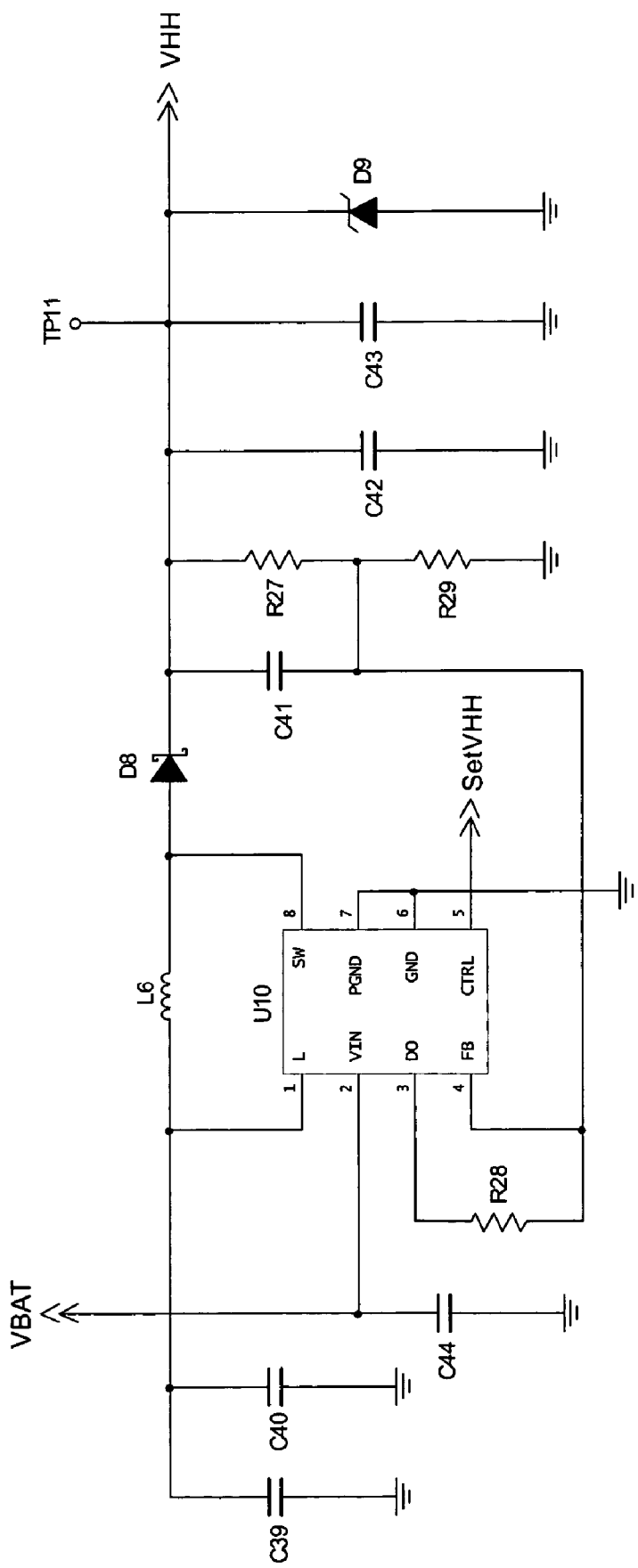
FIG. 22 is a circuit diagram showing a possible circuit for the VHH power supply feature used with the implantable pulse generator shown in FIGS. 7A and 7B.

A circuit diagram showing a desired configuration for the VHH power supply 44 is shown in FIG. 22. It is to be appreciated that modifications to this circuit diagram configuration which produce the same or similar functions as described are within the scope of the invention.

The VHH Power Supply 44 is generally responsible for the following functions:

(1) Provide the Stimulus Output Stage 46 and the Output Multiplexer 48 with a programmable DC voltage between the battery voltage and a voltage high enough to drive the required cathodic phase current through the electrode circuit plus the voltage drops across the stimulator stage, the output multiplexer stage, and the output coupling capacitor. VHH is typically 12 VDC or less for neuromodulation applications; and 25V or less for muscle stimulation applications.

The Components of the VHH Power Supply might include:

(1) Micropower, inductor based (fly-back topology) switch mode power supply (U10); e.g., Texas Instruments TPS61045, Texas Instruments TPS61041, or Linear Technology LT3464 with external voltage adjustment components.

(2) L6 is the flyback energy storage inductor.

(3) C42 & C43 form the output capacitor.

(4) R27, R28, and R29 establish the operating voltage range for VHH given the internal DAC which is programmed via the SETVHH logic command from the microcontroller 24.

(5) Diode D9 serves no purpose in normal operation and is added to offer protection from over-voltage in the event of a VHH circuit failure.

(6) The microcontroller 24 monitors VHH for detection of a VHH power supply failure, system failures, and optimizing VHH for the exhibited electrode circuit impedance.

e. Stimulus Output Stage

The Stimulus Output Stage(s) 46 is responsible for the following functions:

(1) Generate the identified biphasic stimulus current with programmable (dynamically adjustable during use) cathodic phase amplitude, pulse width, and frequency. The recovery phase may incorporate a maximum current limit; and there may be a delay time (most likely a fixed delay) between the cathodic phase and the recovery phase (see FIG. 18). Typical currents (cathodic phase) for neuromodulation applications range between about 100 microamps and about 20 milliamps. For applications using nerve cuff electrodes or other electrodes that are in very close proximity to the excitable neural tissue, stimulus amplitudes of less than one milliamp might be necessary because of this close proximity. Electrode circuit impedances can vary with the electrode and the application, but are likely to be less than 2,000 ohms and greater than 100 ohms across a range of electrode types.

The Components of the Stimulus Output Stage may include:

(1) The cathodic phase current through the electrode circuit is established by a high gain (HFE) NPN transistor (Q7) with emitter degeneration. In this configuration, the collector current of the transistor (Q7) is defined by the base drive voltage and the value of the emitter resistor (R24).

Two separate configurations are possible: In the first configuration (as shown in FIG. 17), the base drive voltage is provided by a DAC peripheral inside the microcontroller 24 and is switched on and off by a timer peripheral inside the microcontroller. This switching function is performed by an analog switch (U8). In this configuration, the emitter resistor (R24) is fixed in value and fixed to ground.

In a second alternative configuration, the base drive voltage is a fixed voltage pulse (e.g., a logic level pulse) and the emitter resistor is manipulated under microcontroller control. Typical options may include resistor(s) terminated by microcontroller IO port pins that are held or pulsed low, high, or floating; or an external MOSFET that pulls one or more resistors from the emitter to ground under program control. Note that the pulse timing need only be applied to the base drive logic; the timing of the emitter resistor manipulation is not critical.

The transistor (Q7) desirably is suitable for operation with VHH on the collector. The cathodic phase current through the electrode circuit is established by the voltage drop across the emitter resistor. Diode D7, if used, provides a degree of temperature compensation to this circuit.

(2) The microcontroller 24 (preferably including a programmable counter/timer peripheral) generates stimulus pulse timing to generate the cathodic and recovery phases and the interphase delay. The microcontroller 24 also monitors the cathode voltage to confirm the correct operation of the output coupling capacitor, to detect system failures, and to optimize VHH for the exhibited electrode circuit impedance; i.e., to measure the electrode circuit impedance. Additionally, the microcontroller 24 can also monitor the pulsing voltage on the emitter resistor; this allows the fine adjustment of low stimulus currents (cathodic phase amplitude) through changes to the DAC value.

f. The Output Multiplexer

The Output Multiplexer 48 is responsible for the following functions:

(1) Route the Anode and Cathode connections of the Stimulus Output Stage 46 to the appropriate electrode based on addressing data provided by the microcontroller 24.

(2) Allow recharge (recovery phase) current to flow from the output coupling capacitor back through the electrode circuit with a programmable delay between the end of the cathodic phase and the beginning of the recovery phase (the interphase delay).

The circuit shown in FIG. 17 may be configured to provide monopolar stimulation (using the case 26 as the return electrode) to Electrode 1, to Electrode 2, or to both through time multiplexing. This circuit could also be configured as a single bipolar output channel by changing the hardwire connection between the circuit board and the electrode; i.e., by routing the CASE connection to Electrode 1 or Electrode 2. The use of four or more channels per multiplexer stage (i.e., per output coupling capacitor) is possible.

The Components of the Output Multiplexer might include:

(1) An output coupling capacitor in series with the electrode circuit. This capacitor is desirably located such that there is no DC across the capacitor in steady state. This capacitor is typically charged by the current flow during the cathodic phase to a voltage range of about ¼th to ¹/₁₀th of the voltage across the electrode circuit during the cathodic phase. Similarly, this capacitor is desirably located in the circuit such that the analog switches do not experience voltages beyond their ground of power supply (VHH).

(2) The analog switches (U7) must have a suitably high operating voltage, low ON resistance, and very low quiescent current consumption while being driven from the specified logic levels. Suitable analog switches include the Vishay/Siliconix DG412HS, for example.

(3) Microcontroller 24 selects the electrode connections to carry the stimulus current (and time the interphase delay) via address lines.

(4) Other analog switches (U9) may be used to sample the voltage of VHH, the CASE, and the selected Electrode. The switched voltage, after the voltage divider formed by R25 and R26, is monitored by the microcontroller 24.

g. Wireless Telemetry Circuit

The Wireless Telemetry circuit 50 is responsible for the following functions:

(1) Provide reliable, bidirectional communications (half duplex) with an external controller, programmer, or an optional charger 34, for example, via a VHF-UHF RF link (likely in the 402 MHZ to 405 MHz MICS band per FCC 47 CFR Part 95 and the Ultra Low Power—Active Medical Implant (AMI) regulations of the European Union). This circuit will look for RF commands at precisely timed intervals (e.g., twice a second), and this function must consume very little power. Much less frequently this circuit will transmit to the external controller. This function should also be as low power as possible; but will represent a lower total energy demand than the receiver in most of the anticipated applications. The RF carrier is amplitude modulated (on-off keyed) with the digital data. Serial data is generated by the microcontroller 24 already formatted and timed. The wireless telemetry circuit 50 converts the serial data stream into a pulsing carrier signal during the transit process; and it converts a varying RF signal strength into a serial data stream during the receive process.

The Components of the Wireless Telemetry Circuit might include:

(1) a crystal controlled, micropower transceiver chip such as the AMI Semiconductor AMIS-52100 (U6). This chip is responsible for generating the RF carrier during transmissions and for amplifying, receiving, and detecting (converting to a logic level) the received RF signals. The transceiver chip must also be capable of quickly starting and stopping operation to minimize power consumption by keeping the chip disabled (and consuming very little power) the majority of the time; and powering up for only as long as required for the transmitting or receiving purpose.

(2) The transceiver chip has separate transmit and receive ports that must be switched to a single antenna/feedthru. This function is performed by the transmit/receive switch (U5) under microcontroller control via the logic line XMIT. The microcontroller 24 controls the operation of the transceiver chip-via an I²C serial communications link. The serial data to and from the transceiver chip may be handled by a UART or a SPI peripheral of the microcontroller. The message encoding/decoding and error detection may be performed by a separate, dedicated microcontroller; else this processing will be time shared with the other tasks of the only microcontroller.

The various inductor and capacitor components (U6) surrounding the transceiver chip and the transmit/receive switch (U5) are impedance matching components and harmonic filtering components, except as follows:

(1) X2, C33 and C34 are used to generate the crystal controlled carrier, desirably tuned to the carrier frequency divided by thirty-two, (2) L4 and C27 form the tuned elements of a VCO (voltage controlled oscillator) operating at twice the carrier frequency, and (3) R20, C29, and C30 are filter components of the PLL (phase locked loop) filter.

B. Lead and Electrode

As previously described, the system 10 includes an implantable pulse generator 18, a lead 12, and an electrode 16. Two possible types of electrodes will be described below, although any number of electrode types may be used.

1. Implantation in Adipose Tissue

Neurostimulation leads and electrodes that may be well suited for implantation in muscle tissue are not well suited for implantation in soft adipose tissue in the targeted location at or near the pubic symphysis. This is because adipose tissue is unlike muscle tissue, and also because the vascularization and innervation of tissue at or near the pubic symphysis is unlike tissue in a muscle mass. Muscular tissue is formed by tough bundles of fibers with intermediate areolar tissue. The fibers consist of a contractile substance enclosed in a tubular sheath. The fibers lend bulk, density, and strength to muscle tissues that are not found in soft adipose tissue. Muscles are also not innervated with sensory nerves or highly vascularized with blood vessels to the extent found in the pubic region of the body.

Figure 23:
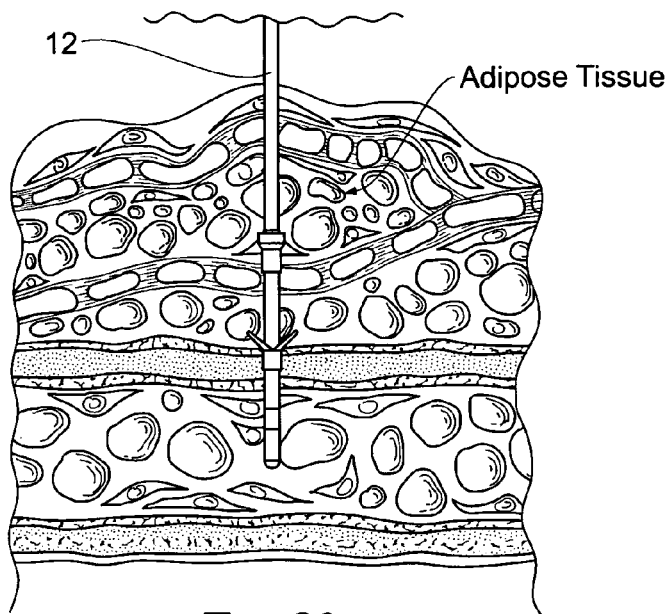
FIGS. 23 and 24 are anatomic section views of the adipose tissue region with one lead and electrode associated with the system shown in FIG. 6, after having been implanted.

Adipose tissue (see FIG. 23) consists of small vesicles, called fat-cells, lodged in the meshes of highly vascularized areolar tissue containing minute veins, minute arteries, and capillary blood vessels. The fat-cells vary in size, but are about the average diameter of ¹/₅₀₀ of an inch. They are formed of an exceedingly delicate protoplasmic membrane, filled with fatty matter, which is liquid during life and turns solid after death. They are round or spherical where they have not been subject to pressure; otherwise they assume a more or less angular outline. The fat-cells are contained in clusters in the areolae of fine connective tissue, and are held together mainly by a network of capillary blood vessels, which are distributed to them.

In one embodiment, the lead 12 and electrode 16 are sized and configured to be inserted into and to rest in soft adipose tissue (see FIG. 23), such as in the lower abdomen for example, without causing pain or discomfort or impact body image. Desirably, the lead 12 and electrode 16 can be inserted using a small (e.g., smaller than 16 gauge) introducer with minimal tissue trauma. The lead 12 and electrode 16 are formed from a biocompatible and electrochemically suitable material and possess no sharp features that can irritate tissue during extended use. Furthermore, the lead 12 and electrode 16 possess mechanical characteristics including mechanical compliance (flexibility) along their axis (axially), as well as perpendicular to their axis (radially), and unable to transmit torque, to flexibly respond to dynamic stretching, bending, and crushing forces that can be encountered within soft, mobile adipose tissue in this body region without damage or breakage, and to accommodate relative movement of the pulse generator 18 coupled to the lead 12 without imposing force or torque to the electrode 16 which tends to dislodge the electrode.

Figure 24:
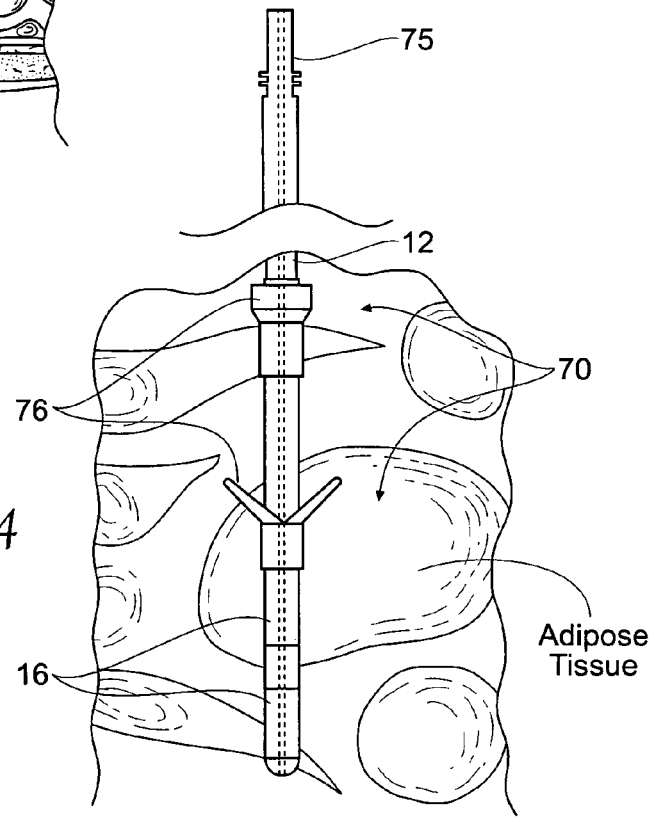

Furthermore, the lead 12 and electrode 16 desirably include an anchoring means 70 for providing retention strength to resist migration within or extrusion from soft, mobile adipose tissue in this body region in response to force conditions normally encountered during periods of extended use (see FIG. 24). In addition, the anchoring means 70 is desirably sized and configured to permit the electrode 16 position to be adjusted easily during insertion, allowing placement at the optimal location where bilateral stimulation of the left and right branches of the genital nerves occurs. The anchoring means 70 functions to hold the electrode at the implanted location despite the motion of the tissue and small forces transmitted by the lead due to relative motion of the connected pulse generator due to changes in body posture or external forces applied to the abdomen. However, the anchoring means 70 should allow reliable release of the electrode 16 at higher force levels, to permit withdrawal of the implanted electrode 16 by purposeful pulling on the lead 12 at such higher force levels, without breaking or leaving fragments, should removal of the implanted electrode 16 be desired.

The lead 12 and electrode 16 is sized and configured to be anchored solely in soft adipose tissue, with no dependence on support or stability from muscle tissue. The lead 12 and electrode 16 are particularly well suited for placement in this soft adipose tissue because of the unique shape, size, spacing, and orientation of the anchoring means 70, which allows the lead 12 and electrode 16 to be used for other indications in addition to sexual restoration, such as in the field of urology (e.g., stimulation of nerves in adipose tissue for the treatment of incontinence).

a. The Lead

Figure 26:
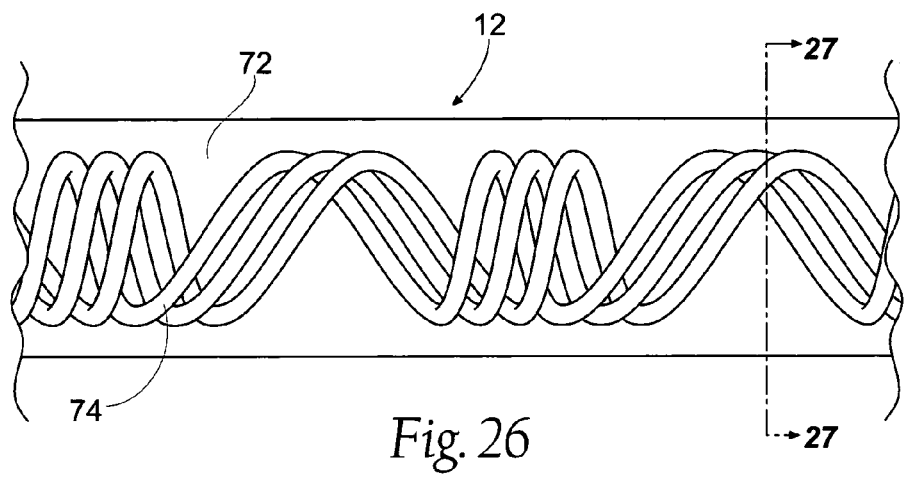
FIG. 26 is a side interior view of a representative embodiment of a lead of the type shown in FIGS. 23 and 24.
Figure 27:
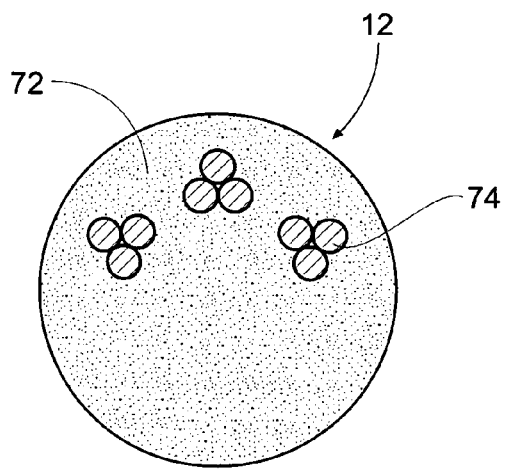
FIG. 27 is an end section view of the lead taken generally along line 27-27 in FIG. 26.

FIGS. 26 and 27 show a representative embodiment of a lead 12 and electrode 16 that provide the foregoing features. The implantable lead 12 comprises a molded or extruded component 72, which encapsulates a coiled stranded wire element 74, and a connector 75 (shown in FIG. 24). The wire element may be trifilar, as shown in FIG. 26, and may be constructed of coiled MP35N nickel-cobalt wire or wires that have been coated in polyurethane. The molded or extruded lead 12 can have an outside diameter as small as about one (1) mm. The lead 12 may be approximately 10 cm to 40 cm in length. The lead 12 provides electrical continuity between the connector 75 and the electrode 16.

The coil's pitch can be constant or, as FIG. 26 shows, the coil's pitch can alternate from high to low spacing to allow for flexibility in both compression and tension. The tight pitch will allow for movement in tension, while the open pitch will allow for movement in compression.

A standard IS-1 or similar type connector 75 at the proximal end provides electrical continuity and mechanical attachment to the IPG. The lead 12 and connector 75 all may include provisions for a guidewire that passes through these components and the length of the lead 12 to the conductive electrode 16 at the distal end.

b. The Electrode

The electrode 16 may comprise one or more electrically conductive surfaces. Two conductive surfaces are show in FIG. 24. The two conductive surfaces can be used either A) as two individual stimulating (cathodic) electrodes in monopolar configuration using the casing 26 of the IPG 18 as the return (anodic) electrode or B) in bipolar configuration with one electrode functioning as the stimulating (cathodic) electrode and the other as the return (anodic) electrode.

In general, bipolar stimulation is more specific than monopolar stimulation—the area of stimulation is much smaller—which is good if the electrode 16 is close to the target nerve N. But if the electrode 16 is farther from the target nerve N, then a monopolar configuration could be used because with the IPG 18 acting as the return electrode, activation of the nerve is less sensitive to exact placement than with a bipolar configuration.

In use, a physician may first attempt to place the electrode 16 close to the target nerve N so that it could be used in a bipolar configuration, but if bipolar stimulation failed to activate the nerve, then the electrode 16 could be switched to a monopolar configuration. Two separate conductive surfaces on the electrode 16 provide an advantage because if one conductive surface fails to activate the target nerve N because it is too far from the nerve, then stimulation with the second conductive surface could be tried, which might be closer to the target nerve N. Without the second conductive surface, a physician would have to reposition the electrode to try to get closer to the target nerve N.

The electrode 16, or electrically conductive surface or surfaces, can be formed from PtIr (platinum-iridium) or, alternatively, 316L stainless steel, and possess a conductive surface of approximately 10 $mm^2$-20 $mm^2$. This surface area provides current densities up to 2 mA/mm2 with per pulse charge densities less than 0.5 µC/mm2. These dimensions and materials deliver a charge safely within the stimulation levels supplied by the IPG.

Each conductive surface has an axial length in the range of about three to five millimeters in length. When two or more conductive surfaces are used, either in the monopolar or bipolar configurations as described, there will be an axial spacing between the conductive surfaces in the range of 1.5 to 2.5 millimeters.

c. The Anchoring Means

Figure 25A:
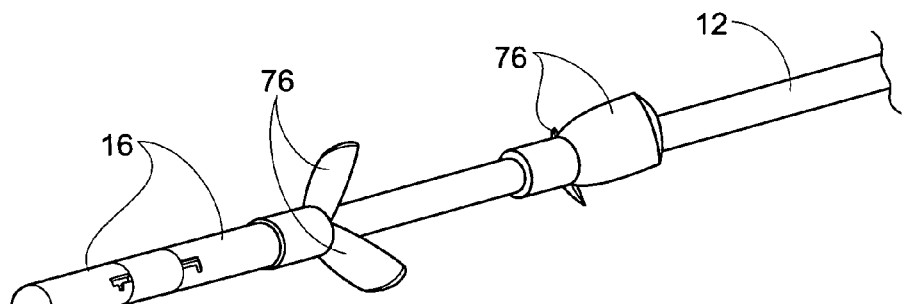
FIGS. 25A and 25B are perspective views of the lead and electrode associated with the system shown in FIG. 6.
Figure 25B:
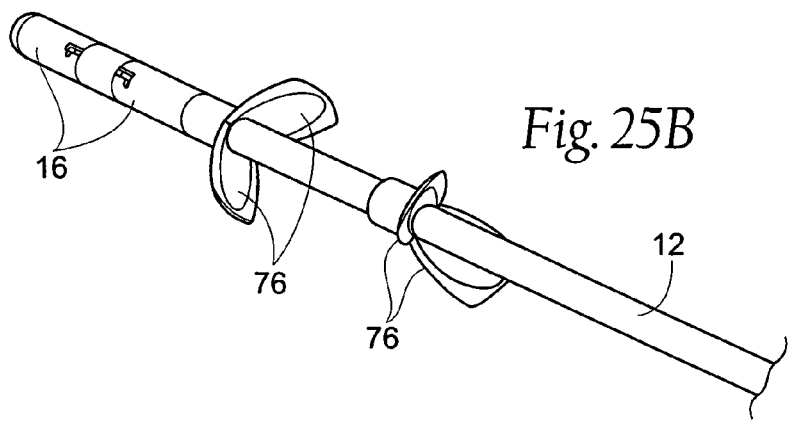

In the illustrated embodiment (see FIGS. 24 and 25), the lead is anchored by anchoring means 70 specifically designed to secure the electrode 16 in the layer of adipose tissue in electrical proximity to the target nerve N, without the support of muscle tissue. The anchoring means 70 takes the form of an array of shovel-like blades or scallops 76 proximal to the proximal-most electrode 16 (although a blade 76 or blades could also be proximal to the distal most electrode 16, or could also be distal to the distal most electrode 16). The blades 76 are desirably present relatively large, generally planar surfaces, and are placed in multiple rows axially along the lead 12. The blades 76 may also be somewhat arcuate as well, or a combination of arcuate and planar surfaces. A row of blades 76 comprises two blades 76 spaced 180 degrees apart. The blades 76 may have an axial spacing between rows of blades in the range of six to fourteen millimeters, and each row may be spaced apart 90 degrees. The blades 76 are normally biased toward a radially outward condition into tissue. In this condition, the large surface area and orientation of the blades 76 allow the lead 12 to resist dislodgement or migration of the electrode 16 out of the correct location in the surrounding tissue. In the illustrated embodiment, the blades 76 are biased toward a proximal-pointing orientation, to better resist proximal migration of the electrode 16 with lead tension. The blades 76 are desirably made from a polymer material, e.g., high durometer silicone, polyurethane, or polypropylene, bonded to or molded with the lead 12.

The blades 76 can be deflected toward a distal direction in response to exerting a pulling force on the lead 12 at a threshold axial force level, which is greater than expected day-to-day axial forces. The blades 76 are sized and configured to yield during proximal passage through tissue in result to such forces, causing minimal tissue trauma, and without breaking or leaving fragments, despite the possible presence of some degree of tissue in-growth. This feature permits the withdrawal of the implanted electrode 16, if desired, by purposeful pulling on the lead 12 at the higher axial force level.

Desirably, the anchoring means 70 is prevented from fully engaging body tissue until after the electrode 16 has been deployed. The electrode 16 is not deployed until after it has been correctly located during the implantation (installation) process.

Figure 28:
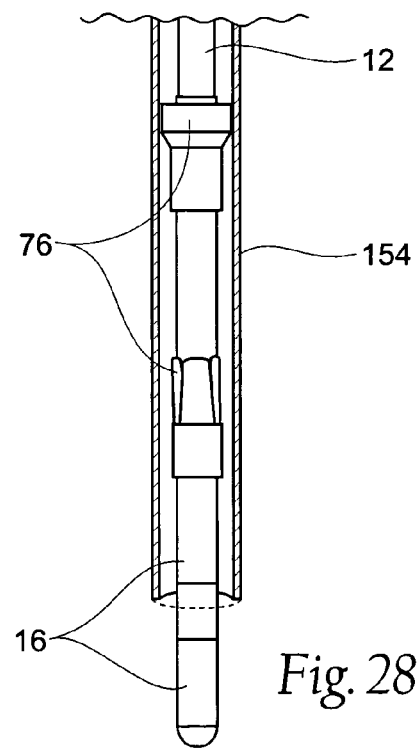
FIG. 28 is an elevation view, in section, of a lead and electrode of the type shown in FIGS. 23 and 24 residing within an introducer sheath for implantation in a targeted tissue region, the anchoring members being shown retracted within the sheath.
Figure 40:
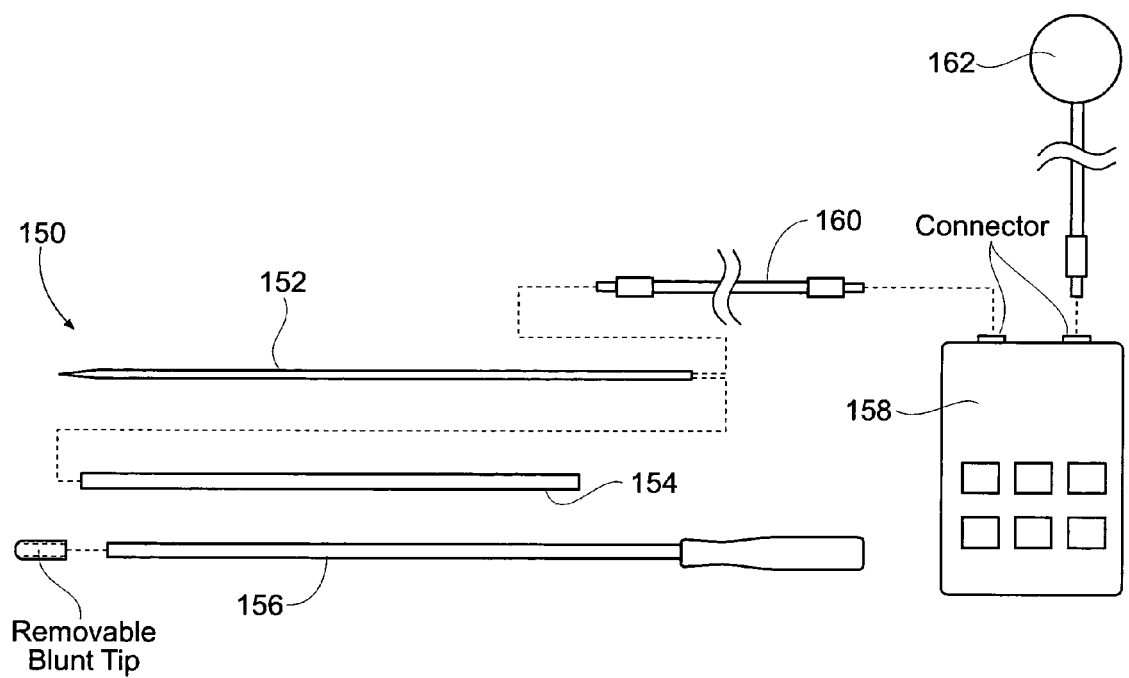
FIG. 40 is a plane view of a system of surgical tools that can be use to implant the system shown in FIG. 6.
Figure 41:
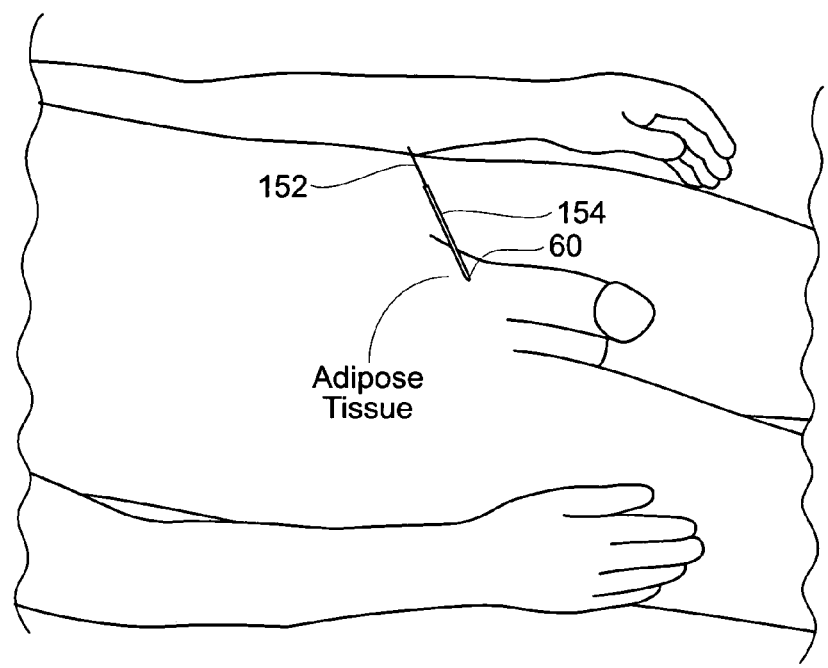
FIGS. 41 through 44 illustrate general steps of implanting the system shown in FIG. 6 in either a single surgical procedure or two surgical procedures.
Figure 42:
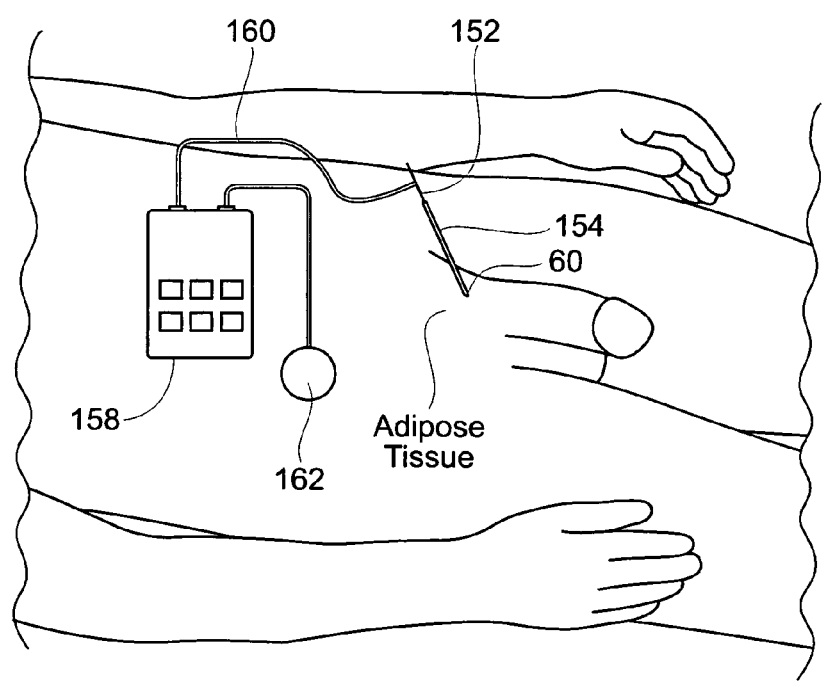

More particularly, and as will be described in greater detail later, the lead 12 and electrode 16 are intended to be percutaneously introduced through a sleeve 154 shown in FIG. 40 (this is also shown in FIGS. 41 and 42). As shown in FIG. 28, the blades 76 assume a collapsed condition against the lead 12 body when within the sleeve 154. In this condition, the blades 76 are shielded from contact with tissue. Once the location is found, the sleeve 154 can be withdrawn, holding the lead 12 and electrode 16 stationary. Free of the sleeve 154, the blades 76 spring open to assume their radially deployed condition in tissue, fixing the electrode 16 in the desired location.

The position of the electrode 16 relative to the anchoring means 70, and the use of the sleeve 154, allows for both advancement and retraction of the electrode delivery sleeve 154 during implantation while simultaneously delivering test stimulation. The sleeve 154 can be drawn back relative to the lead 12 to deploy the electrode 16 anchoring means 70, but only when the physician determines that the desired electrode location has been reached. The withdrawal of the sleeve 154 from the lead 12 causes the anchoring means 70 to deploy without changing the position of electrode 16 in the desired location (or allowing only a small and predictable, set motion of the electrode). Once the sleeve 154 is removed, the flexible, silicone-coated or polyurethane-coat lead 12 and electrode 16 are left implanted in the tissue.

2. Molded Nerve Cuff

Figure 29:
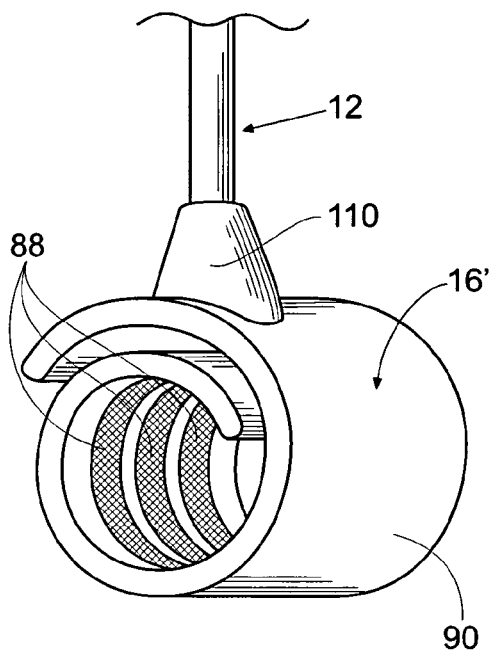
FIG. 29 is a perspective view of a molded cuff electrode prior to implantation.
Figure 31:
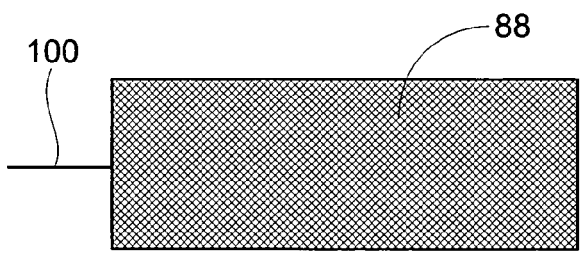
FIGS. 31 and 32 are plan views showing both solid and segmented embodiments for the electrically conductive surface.
Figure 32:
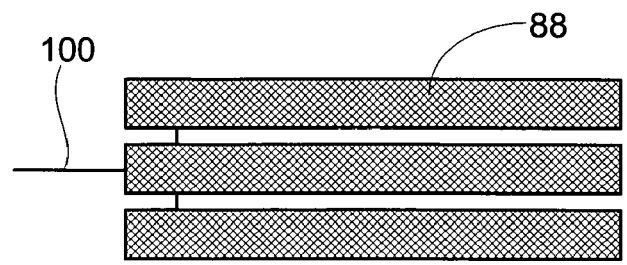

In an alternative embodiment, a lead 12 and a cuff electrode 16' may be used. As FIG. 29 shows, the cuff electrode 16' includes at least one electrically conductive surface 88. In the illustrated embodiment, there are three individually controllable electrically conductive surfaces 88, although more or less may be used. The surface 88 may be solid, as shown in FIG. 31, or the surface may be segmented into isolated conductive segments electrically coupled by a wire, as shown in FIG. 32. It is to be appreciated that additional alternative configurations are possible as well.

In this arrangement, the lead 12 (see FIG. 33) comprises a molded component 98, which encapsulates a coiled trifilar stranded wire element 100. Each wire of the element 100 is coupled to one of the electrically conductive solid or segmented surfaces 88. These surfaces may be manufactured using a thin film of metal deposited on a liquid crystal polymer substrate, or from strips of platinum, for example.

As FIG. 29 shows, the cuff electrode 16' comprises a body 90 that may be molded from a low durometer elastomer material 106 (e.g., silicone, such as a two part, translucent, pourable silicone elastomer, e.g., Nusil MED-4211). The electrically conductive surfaces 88 are integrated with the body 90 during the molding process. Additional alternative configurations of segmented conductive surfaces and the molding process of the cuff electrode 16' is described in co-pending U.S. patent application Ser. No. 11/196,995, filed 4 Aug. 2005 and entitled "Devices, Systems, and Methods Employing a Molded Nerve Cuff Electrode," which is incorporated herein by reference.

Figure 33:
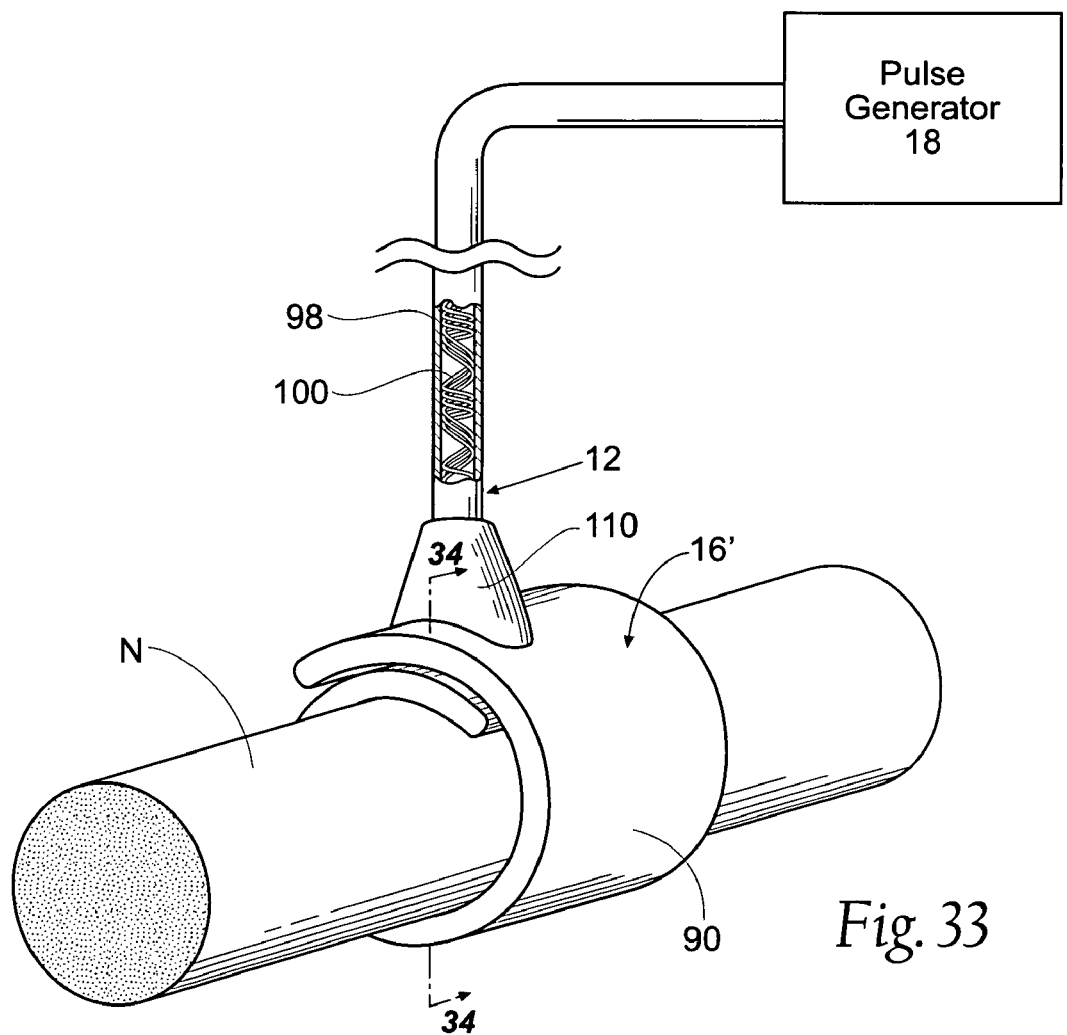
FIG. 33 is a perspective, diagrammatic view of the molded cuff electrode shown in FIG. 29 implanted about a nerve and coupled to a pulse generator to deliver a neuromodular stimulation to achieve a desired therapeutic result.
Figure 34:
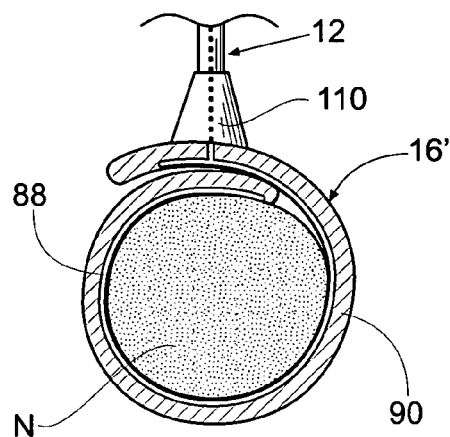
FIG. 34 is a side section view of the molded cuff electrode taken generally along line 34-34 on FIG. 33.

The molded body 90 of the cuff electrode 16' is shaped or formed during the molding process to normally assume a curled or tubular spiral or rolled configuration. As shown in FIG. 29, in its normal coiled condition, the body 90 extends in a spiral having a range of about 450 degrees to about 560 degrees from end to end, and in one embodiment about 540 degrees from end to end. The body 90 can be elastically uncoiled to increase its inner diameter (as FIGS. 33 and 34 show), e.g., to be initially fitted about the periphery of the target nerve N, and in response to post-operative changes in the diameter of the target nerve N that might occur due to swelling. The elasticity of the body 90 wraps the electrically conductive surfaces snugly against the periphery of the targeted nerve N. The elasticity of the body 90 is selected to snugly wrap about the target nerve N without causing damage or trauma. To this end, it is believed desirable that the elastic memory of the cuff electrode 16' exhibits a predictable and repeatable pressure vs. diameter relationship that gradually increases pressure with increase in diameter to allow the electrode to fit snuggly about the periphery of a nerve, but not too tightly to cause damage (i.e., exerts a maximum pressure about the target nerve N that does not exceed about 20 mmHg).

Figure 30:
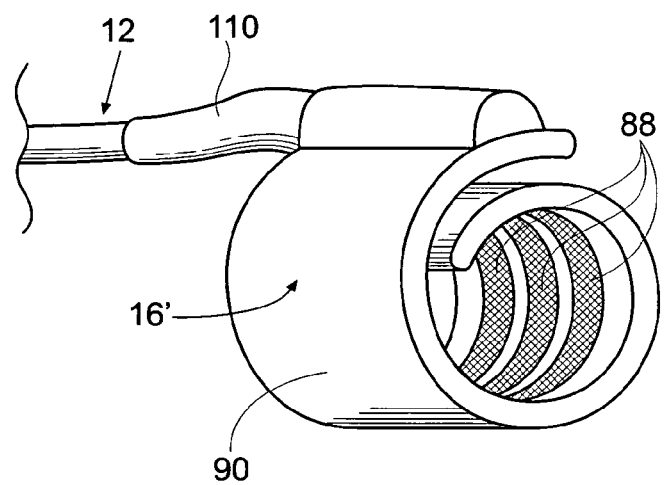
FIG. 30 is a perspective view of an alternative embodiment of the molded cuff electrode shown in FIG. 29, showing the lead extending generally parallel from the cuff electrode.

As FIG. 29 shows, the electrode 16', being a molded component, desirably includes a molded or over-molded section forming a strain relief boot 110 at the junction between the lead 12 and the cuff body 90. The boot 110 strengthens the junction, to resist the effect of torque forces that might be applied during implantation and use along the lead 12. In addition, the strain relief boot 110 helps to prevent tension and/or motion from damaging the lead to cuff interface for a longer flex life. FIG. 30 shows an alternative embodiment where the lead 12 and strain relief boot 110 are generally parallel to the cuff body 90. The strain relief boot 110 may take on any desired shape (i.e., coiled, bent, cone, or zigzag) to aid in its strain relief properties and to improve manufacturability. It is to be appreciated that the lead to cuff interface may be at any desired angle and is not limited to a parallel or perpendicular configuration.

Figure 35:
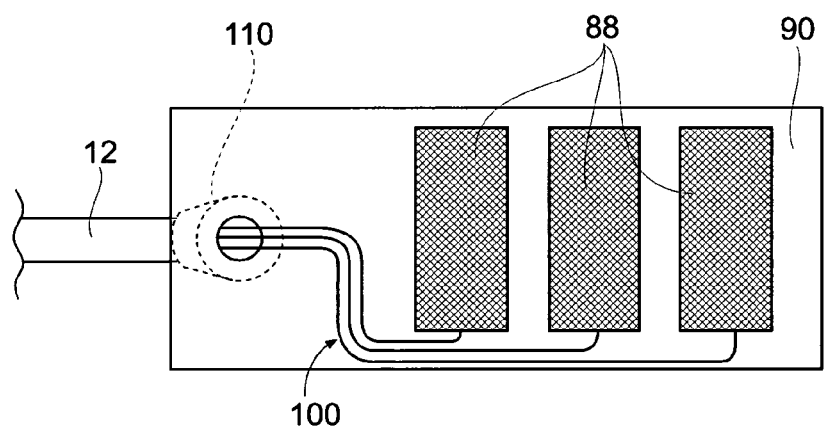
FIG. 35 is a plan view of an alternative embodiment of the conductive surfaces configuration.
Figure 36:
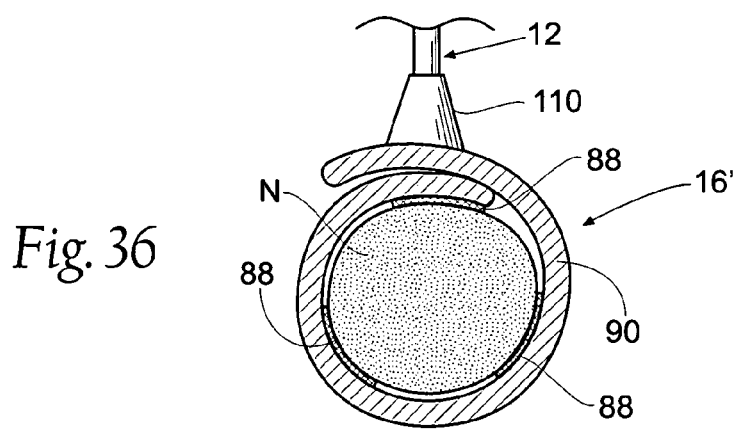
FIG. 36 is a side section view of the alternative embodiment shown in FIG. 35 positioned about a nerve N.

As FIG. 34 shows, when wrapped about the target nerve N, the electrically conductive surfaces 88 make and sustain circumferential contact substantially about the entire periphery of the target nerve N. In an alternative embodiment shown in FIGS. 35 and 36, the electrically conductive surfaces 88 may be positioned so as to make contact with the target nerve N along the axis of the nerve, and around only a portion of the circumference of the target nerve N. FIG. 35 shows an uncoiled cuff body 90 including three electrically conductive surfaces 88. FIG. 36 shows the conductive surfaces 88 positioned along a length (the axis) of the target nerve N.

In a representative embodiment, the body 90 possesses a minimum diameter (when in its normally coiled condition) of as small as one (1) mm, which makes it well suited for implantation about small nerves. The minimum diameter of the body 90 can, of course, be molded to possess larger minimum diameters, to provide a family of nerve cuff electrodes 16' of different diameters that accommodate the range of diameters of human and animal nerves, from small to large.

The electrically conductive surfaces 88 are made, e.g., from strips of platinum, either as one long strip, or as segmented strips that are connected to each other by at least one wire. In addition, these or alternative configurations may be manufactured using a thin film of metal deposited on a liquid crystal polymer substrate. The electrically conductive surface 88 measures at least one mm of length along the axis of the target nerve N and at least one mm of width along the circumference of the target nerve N. In one representative embodiment, the strips 88 each measure about 10 mm×2 mm×0.0254 mm in length, width, and thickness, respectively. The geometry allows the molded elastomeric body 90 to securely hold the strips without migration, with the surfaces 88 exposed for contact with the nerve. In the illustrated embodiment, the electrically conductive surfaces 88 are carried in an exposed array circumferentially against and along the axis of the target nerve N. This geometry is well suited for applying neuromodulation stimulation, as well as nerve conduction blocks, and has application for use in other indications as well. Other geometries and configurations can, of course, be used for other indications.

a. Implanting the Nerve Cuff

Due to its mechanical and physical properties, the molded cuff electrode 16' shown in FIG. 29 is, in use, well suited for placement about a peripheral nerve to deliver a neuromodulation stimulation. This is because the electrode 16' (i) reliably establishes and maintains circumferential contact about substantially the entire nerve periphery, (ii) exhibits a predictable and repeatable diameter vs. pressure curve, (iii) is adaptive to post-operative swelling, and (iv) resists the effects of translational and rotational forces to stay in place post-operatively.

i. Implant Applicator Tool

Figure 37:
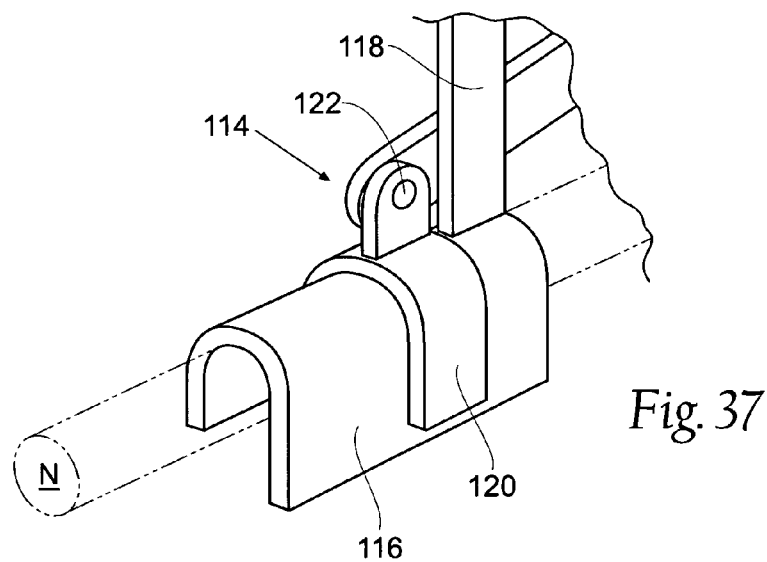
FIG. 37 is an applicator tool for placement of a molded cuff electrode of the type shown in FIG. 29 about a nerve, the applicator tool being shown before mounting of the electrode with the electrode delivery mechanism in an aft condition.
Figure 38:
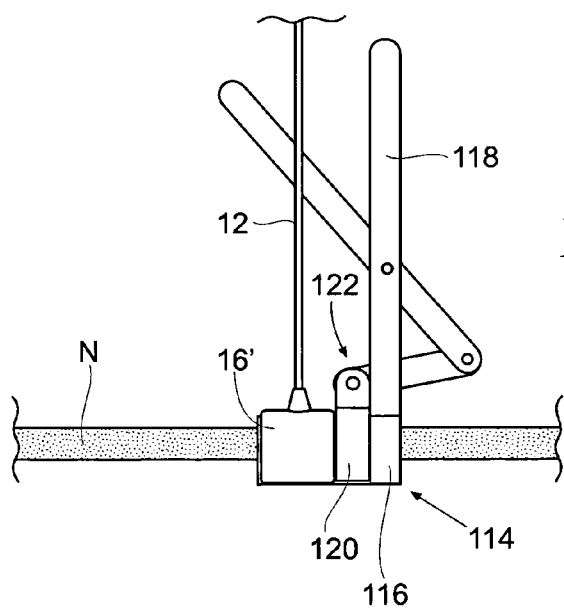
FIG. 38 is a side view of the applicator tool shown in FIG. 37, with the electrode mounted and the electrode delivery mechanism in an aft condition, ready to implant the electrode about a nerve.
Figure 39:
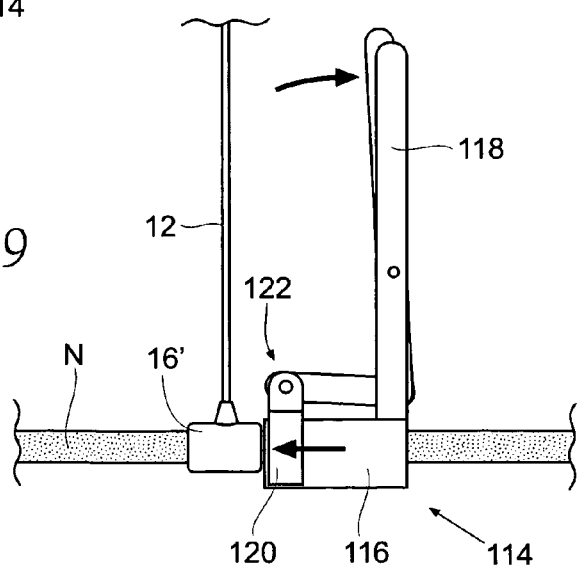
FIG. 39 is a side view of the applicator tool shown in FIG. 37, with the electrode delivery mechanism translated to a forward condition to implant the electrode about a nerve.

As shown in FIGS. 37 to 39, the implantation of the electrode 16' can be facilitated by use of an applicator tool 44. While tools of various configurations can be used, the applicator tool 114 shown in FIGS. 37 to 39 includes an applicator body 116 with a handle 118. As FIG. 37 shows, the applicator body 116 comprises an open ended, inverted trough for fitment over a portion of a target nerve N. As will be described later, the curvilinear form of the body 116 accommodates mounting of the electrode 16' in an uncoiled condition.

The applicator tool 114 also includes a slider 120 carried on the body 116. The slider 120 moves along the axis of the body 116 between a forward position (FIG. 39) and an aft position (FIG. 38). A scissors-type linkage 122 is coupled to the handle 118 so an operator can easily affect movement of the slider 120 fore and aft. Opening the linkage 122 moves the slider 120 aft (see FIG. 38); closing the linkage 122 moves the slider forward (see FIG. 39).

The inverted trough shape of the applicator body 116 is sized and configured so that, when the slider 120 is in is aft position, the electrode 16' can be uncoiled and mounted on the body 116 forward of the slider 120, as FIG. 38 shows. This is desirably accomplished immediately before placing the applicator tool 114 in the targeted position on the target nerve N, which is shown in FIG. 38.

Closing the linkage 122 (as FIG. 39 shows), moves the slider 120 forward. The slider pushes against the electrode 16' and ultimately ejects the electrode 16' from the applicator body 116 onto the target nerve N (as FIG. 39 shows). Free of the trough-shaped applicator body 116, the elastic memory of the molded electrode 16' causes it to coil about the target nerve N, as FIGS. 33 and 34 show. The applicator tool 114 can now be removed from the target nerve N, leaving the electrode 16' implanted about it.

The applicator tool 114 can be formed of a metal or plastic material. Desirably, the tool 114 is molded from snap together medical grade plastic parts (e.g., polystyrene), and is supplied as part of a sterile kit with the electrode 16' as a single-use device.

The applicator tool 114 makes possible a straightforward and reliable placement of the electrode 16' into humans and animals, e.g., installation in vivo desirably is accomplished in one minute or less.

III. Implant Tools

The implant system 10 shown in FIG. 6 makes desirable a system of physician surgical tools (shown in FIG. 40) to facilitate implantation of the implant system 10 in the intended way, desirably on an outpatient basis.

The surgical tool system 150 shown in FIG. 40 includes a needle 152 (or trocar) and a companion introducer sleeve 154. The sleeve 154 is electrically insulated or insulated except at its tip. The needle 152 is also electrically insulated, except at its tip. The tool system 150 also includes a tunneling tool 156.

The tool system 150 also includes an external pulse generator 158, which operates to generate stimulation wave pulses of the same type as the implanted pulse generator 18. The external pulse generator 158 includes a connector cable 160 to couple the pulse generator 158 to the needle 152. A patch electrode 162 is also included, which is to be placed on the skin of the individual and coupled to the external pulse generator 158, to serve as a return path for the stimulation waveforms.

Using the surgical tool system 150, the implant system 10 can be implanted in the manner shown in FIGS. 8A and 8B.

In the above description, the surgical tool system 150 is used to implant the implant system 10 in a single surgical procedure. Alternatively, and desirably, a two-stage surgical procedure can be used.

The first stage comprises a screening phase that performs test stimulation using a temporary external pulse generator to evaluate if an individual is a suitable candidate for extended placement of the implantable pulse generator. The first stage can be conducted, e.g., during a nominal two week period. If the patient is a suitable candidate, the second stage can be scheduled, which is the implantation of the pulse generator 18 itself, as described below.

IV. Implantation Methodology

Representative surgical techniques will now be described to place the system 10 in a desired location. Additional representative surgical techniques can be used as described in co-pending U.S. patent application Ser. No. 11/149,654, filed 10 Jun. 2005 and entitled "Systems and Methods for Bilateral Stimulation of Left and Right Branches of the Dorsal Genital Nerves to Treat Dysfunctions Such as Urinary Incontinence," which is incorporated herein by reference. The electrode 16 and lead 12 are placed at the targeted tissue site (e.g., in adipose tissue at or near the pubic symphysis), and the IPG 18 is placed remote from the targeted tissue site. It is this desired placement of the lead 12 and electrode 16 that makes possible the bilateral stimulation of both left and right branches of the dorsal genital nerves with a single lead 12 to provide sexual restoration (e.g., erectile restoration).

Before implantation, it is recommended that an oral broad spectrum antibiotic is given and continued for five days. The lower abdomen from the pubic symphysis to umbilicus and from the anterior iliac spines bilaterally are prepped with Betadine (or Hibiclens Solutions for cases of Betadine allergy).

As before generally described, implantation of the implant system 10 shown in FIG. 6 can entail a single surgical procedure or optionally a two-step surgical procedure.

A. Single Surgical Procedure

The site for the needle puncture 60 is located midline or near-midline, near the inferior border of the pubic symphysis aiming toward the base of the penis (or clitoris in females). Local anesthesia (e.g., 1% Lidocaine (2-5 ccs) or equivalent) is injected prior to making the anticipated needle 152 puncture site.

Once local anesthesia is established, as shown in FIG. 41, the needle 152 is placed tip-first into the sleeve 154 and the needle 152 and sleeve 154 are advanced percutaneously into the anesthetized site 60 to a depth necessary to reach the target site between the pubic symphysis and the base of the penis (into the pelvis 4-6 cm rostral to the crus at the base of the penis in proximity to dorsal genital nerve). As FIG. 42 shows, the needle 152 is coupled to the external pulse generator 158 (via the cable 160), to apply stimulation waveforms through the needle tip concurrent with positioning of the needle 152. A patch electrode 162 placed on the skin of the individual is also coupled to the external pulse generator 158 to serve as a return path for the stimulation waveforms.

The physician monitors patient-reported sensation or visible movement of related organs, such as the penis, scrotum, or anal sphincter, (or clitoris for women), in concert with applying stimulation waveforms through the needle tip, penetrating and withdrawing the needle 152 as necessary in a minimally invasive way, until a subcutaneous location where optimal intended stimulation results are realized (e.g., bilateral stimulation of both left and right branches of the genital nerves).

Figure 43:
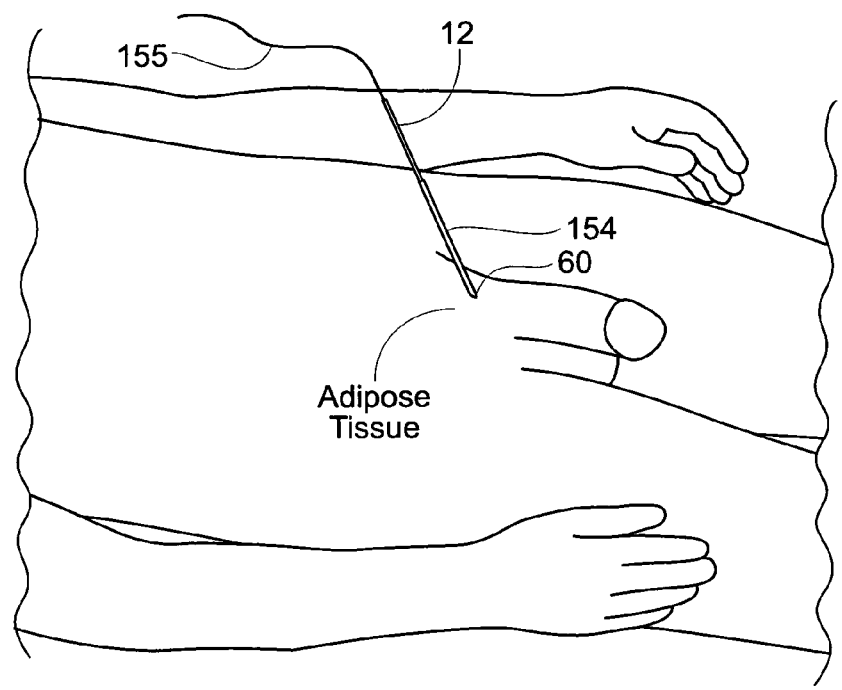

When the desired response is achieved, the needle 152 is removed leaving the sleeve 154 in place. The lead 12 is then inserted into the sleeve 154. The lead 12 is fed into the sleeve 154 using a guidewire 155 down the center of the lead 12 (see FIG. 43). A visual marking on the outside of the lead 12 confirms it is fully inserted into the sleeve 154. The guidewire is then withdrawn from the lead 12. Test stimulation is delivered via the lead 12 to confirm proper location. The sleeve 154 is then removed, leaving the lead 12 anchored in place. Confirmatory stimulation can again be applied to the lead 12.

Figure 44:
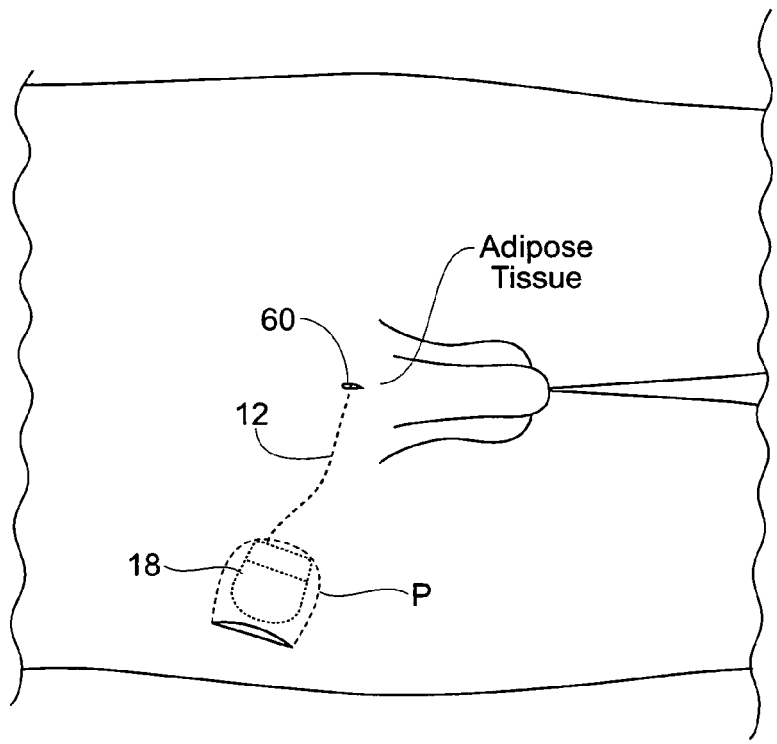

Next, a subcutaneous pocket P is made and sized to accept the implantable pulse generator 18. The pocket P is formed remote from the electrode 16. The puncture site 60 where the lead 12 exits the skin is slightly enlarged with a scalpel. The tunneler 156 is then inserted into the IPG site P and subcutaneously passed through tissue to the lead exit site 60. The lead 12 is inserted into the tunneler 156 and the lead 12 is passed under the skin to the IPG site P, where its connector is mated to the IPG connector. The IPG 18 and the attached lead 12 are then inserted into the subcutaneous pocket P (see FIG. 44) and the incisions at both the pocket P and the lead site 60 are then sutured closed.

B. Two Stage Surgical Procedure

As before described, the first stage installs the electrode 16 and lead 12 in the manner described above, and connects the lead 12 to a temporary external pulse generator 158. If the use of the external pulse generator 158 achieves the desired results after a predefined test period (e.g., two weeks), a pulse generator 18 is implanted in the second stage in the manner described above.

When the procedure is completed, the stimulus parameters for therapy can be programmed into the IPG 18 by the clinician using the clinician programmer 36. As previously described, the clinician programmer 36 may be a Palm-based device that uses wireless communication to program the patient's stimulus parameters up to two meters away from the IPG 18 (see FIG. 12). Stimulus parameters (amplitude, pulse duration, frequency, duty cycle, etc.) are programmed to elicit the erection and be comfortable to the patient. The patient may turn the IPG 18 On or Off using the patient controller, as previously described.

The various tools and devices as just described can be consolidated for use in a functional kit or kits. The kits can take various forms. A single kit may include the necessary components for carrying out a single stage implant procedure as previously described. Alternatively, more than one kit may be constructed for carrying out the two stage implant procedure. Each kit also preferably includes directions for using the contents of the kit to carry out a desired procedure. The instructions for use can also be available through an internet web page.

V. Representative Indications

Due to its technical features, the implant system 10 can be used to provide beneficial results in diverse therapeutic and functional restorations indications.

For example, in the field of urology, possible indications for use of the implant system 10 include the treatment of (i) urinary and fecal incontinence; (ii) micturition/retention; (iii) pelvic floor muscle activity; and/or (iv) pelvic pain; (v) defecation/constipation; and (vi) restoration of sexual function.

Restoration of sexual function pertains to both male and females. Male restoration may include both erection and/or ejaculation actions, for example. Female restoration may include both arousal (engorgement) and/or lubrication, for example.

The implant system 10 can be used for veterinary uses. The ability to control/activate sexual actions such as erection and/or ejaculation actions may be used in animal reproduction technologies, such as artificial insemination. Artificial insemination is commonly used for selective reproduction of bovines, swine, dogs, and cats, as non-limiting examples.

The implant system 10 can be used for deep brain stimulation in the treatment of (i) Parkinson's disease; (ii) multiple sclerosis; (iii) essential tremor; (iv) depression; (v) eating disorders; (vi) epilepsy; and/or (vii) minimally conscious state.

The implant system 10 can be used for pain management by interfering with or blocking pain signals from reaching the brain, in the treatment of, e.g., (i) peripheral neuropathy; and/or (ii) cancer.

The implant system 10 can be used for vagal nerve stimulation for control of epilepsy, depression, or other mood/psychiatric disorders.

The implant system 10 can be used for the treatment of obstructive sleep apnea.

The implant system 10 can be used for gastric stimulation to prevent reflux or to reduce appetite or food consumption.

The implant system 10 can be used in functional restorations indications such as the restoration of motor control, to restore (i) impaired gait after stroke or spinal cord injury (SCI); (ii) impaired hand and arm function after stroke or SCI; (iii) respiratory disorders; (iv) swallowing disorders; (v) sleep apnea; and/or (vi) neurotherapeutics, allowing individuals with neurological deficits, such as stroke survivors or those with multiple sclerosis, to recover functionally.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

Various features of the invention are set forth in the following claims.

We claim:

1. A method comprising
providing a stimulation electrode assembly sized and configured for placement in an adipose tissue region to stimulate a nerve in the adipose tissue region comprising
an elongated lead sized and configured to be implanted within the adipose tissue region at a pubic symphysis, the lead including at least two electrically conductive portions to apply electrical stimulation to nerve tissue in the adipose tissue region, and at least two expandable anchoring structures deployable from the lead to engage adipose tissue and resist dislodgment and/or migration of the at least two electrically conductive portions within the adipose tissue region,
implanting the stimulation electrode assembly in an adipose tissue region at a pubic symphysis, and
conveying electrical stimulation waveforms through the stimulation electrode assembly to achieve selective stimulation of at least one nerve in the adipose tissue region.

2. A method according to claim 1, wherein the stimulation stimulates a left and/or right branch of the dorsal genital nerves.

3. The method according to claim 1, wherein the selective stimulation provides sustainable erections.

4. The method according to claim 1, wherein the step of implanting the stimulation electrode assembly comprises inserting a sleeve in the tissue near the inferior border of the pubic symphysis.

5. The method according to claim 4, wherein the sleeve is aiming towards the base of the penis.

6. The method according to claim 4, wherein the sleeve is aiming towards the base of the clitoris.

7. The method according to claim 4, wherein the step of implanting the stimulation electrode assembly further comprises inserting the lead into the sleeve.

8. The method according to claim 7 further comprising providing test stimulation to the lead to confirm proper placement of the lead.

9. The method according to claim 7 further comprising removing the sleeve.

10. The method according to claim 9 further comprising providing test stimulation to the lead once again to confirm the location of the lead.

11. A method comprising the steps of:
providing a system comprising
a stimulation electrode sized and configured to be implanted in adipose tissue to stimulate the target nerve in a region at a pubic symphysis, the stimulation electrode comprising an elongated lead sized and configured to be implanted within the adipose tissue region, the lead including at least two electrically conductive portions to apply electrical stimulation to nerve tissue in the adipose tissue region, and at least two expandable anchoring structures deployable from the lead to engage adipose tissue and resist dislodgment and/or migration of the at least two electrically conductive portions within the adipose tissue region, and
an implantable pulse generator sized and configured to be positioned subcutaneous to a tissue surface remote from the stimulation electrode, the implantable pulse generator comprising wireless telemetry circuitry, the wireless telemetry circuitry being functional within arms reach of the patient, and being adapted for programming and interrogation of the implantable pulse generator,
implanting the stimulation electrode in an adipose tissue region at a pubic symphysis, and implanting the pulse generator.

12. The method according to claim 11, wherein the step of implanting the stimulation electrode comprises inserting a sleeve in the tissue near the inferior border of the pubic symphysis.

13. The method according to claim 12, wherein the sleeve is aiming towards the base of the penis.

14. The method according to claim 12, wherein the sleeve is aiming towards the base of the clitoris.

15. The method according to claim 12, wherein the step of implanting the stimulation electrode further comprises inserting the lead into the sleeve.

16. The method according to claim 15 further comprising providing test stimulation to the lead to confirm proper placement of the lead.

17. The method according to claim 15 further comprising removing the sleeve.

18. The method according to claim 17 further comprising providing test stimulation to the lead once again to confirm the location of the lead.

* * * * *